United States Patent [19]
Grotendorst et al.

[11] Patent Number: 6,150,101
[45] Date of Patent: Nov. 21, 2000

[54] METHODS OF IDENTIFYING A COMPOSITION THAT ALTERS CONNECTIVE TISSUE GROWTH FACTOR EXPRESSION

[75] Inventors: Gary R. Grotendorst, Miami, Fla.; Douglass M. Bradham, Jr., Baltimore, Md.

[73] Assignee: University of South Florida, Tampa, Fla.

[21] Appl. No.: 09/054,274

[22] Filed: Apr. 2, 1998

Related U.S. Application Data

[60] Division of application No. 08/459,717, Jun. 2, 1995, Pat. No. 5,770,207, which is a continuation-in-part of application No. 08/386,680, Feb. 10, 1995, Pat. No. 5,585,270, which is a division of application No. 08/167,628, Dec. 14, 1993, Pat. No. 5,408,040, which is a continuation of application No. 07/752,427, Aug. 30, 1991, abandoned.

[51] Int. Cl.$^7$ ................................... C12N 15/63
[52] U.S. Cl. ......................... 435/6; 435/69.1; 536/24.1; 935/34
[58] Field of Search ............... 435/6, 7.21, 69.1, 435/69.4, 69.7; 935/34, 36, 9, 10; 536/23.5, 23.51, 24.1

[56] References Cited

U.S. PATENT DOCUMENTS

| | | |
|---|---|---|
| 5,149,691 | 9/1992 | Rutherford . |
| 5,356,630 | 10/1994 | Laurencin et al. . |
| 5,399,361 | 3/1995 | Song et al. . |
| 5,408,040 | 4/1995 | Grotendorst et al. . |

FOREIGN PATENT DOCUMENTS

| | | |
|---|---|---|
| 93/00430 | 1/1993 | WIPO . |

OTHER PUBLICATIONS

Igarashi et al., "Regulation of Connective Tissue Growth Factor Gene Expression in Human Skin Fibroblast and During Wound Repair," *Molecular Biology of the Cell*, vol. 4:637–645, Jun. 1993.

Ryseck et al., "Structure, Mapping, and Expression of fisp–12 a Growth Factor–Inducible Gene Encoding a Secreted Cysteine–Rich Protein," *Cell Growth & Differentiation*, vol. 2:225–233, May 1991.

Shimokado et al., *Cell*, 43:277–286, Nov. 1985.

Campochiaro et al., *Exp. Eye Res.*, 49:217–227, 1989.

Matsuoka et al., *Proc. Natl. Acad. Sci.*, 86:4416–4420, Jun. 1989.

Bradham et al., "Connective Tissue Growth Factor: a Cysteine–rich Mitogen Secreted by Human Vascular Endothelial cells is Related to the SRC–induced Immediate Early Gene Product CEF–10," *J. Cell Biology*,114(6): 1285–1294 (1991).

Oemar et al., "Connective Tissue Growth Factor, Friend or Foe?" *Arteriosclerosis, Thrombosis, and Vascular Biology*, 17(8): 1483–1489 (1997).

*Primary Examiner*—Lorraine Spector
*Attorney, Agent, or Firm*—Gray Cary Ware & Freidenrich LLP; Lisa A. Haile

[57] ABSTRACT

The present invention provides a novel polypeptide, Connective Tissue Growth Factor (CTGF), polynucleotides encoding CTGF, and including 5' and 3' untranslated nucleotides, antibodies reactive with CTGF and means for producing CTGF. Also provided are diagnostic and therapeutic methods for using CTGF, as well as an assay for identifying compositions which affect the expression of CTGF polynucleotide. The invention provides a novel TGF-β responsive element upstream of the polynucleotide encoding CTGF structural gene.

9 Claims, 19 Drawing Sheets

EXONS

AMINO ACIDS

LUCIFERASE EXPRESSION (Photons x $10^{-6}$)

| SEQUENCE USED | BASEL EXP. | TGF-β INDUCED | FOLD INDUCTION |
|---|---|---|---|
| NATIVE<br>GTGTCAAGGGGTC | 0.42 ± 0.01 | 28.0 ± 0.9 | 66.7 (100) |
| GTGTCAAGGtGTC | 0.41 ± 0.05 | 5.7 ± 0.3 | 13.9 (14) |
| GTGTtAAGGGGTC | 0.36 ± 0.03 | 13.2 ± 1.1 | 36.8 (55) |

\* \* \* \*\*\*\* \* BASES MAPPED BY METHYLATION INTERFERENCE

-823 CTGF
TCTAGAGCTCGGCGCGGAGCTCTAATACGACTCACTATAGGGCGTCGACTCGATCCCTTTT--TCTGGAAACATT
*  * *  * *** *  * **** * ***
TCT--TTCT-TCTCCCACTATATTCCCTGACAC--TTAGGCTTCTGAAGATAGCCATTGGTCTGAACTCATA

-706 CTGF
TATTAAG--AGAAAACTAA-----GCA---AGAGTTTTTGGAAATCTGCCCCCAGGAGACTGCATCCTGAGTCAC
* * ** * *  **  *** *  *****
CCTGGACCCCTGAAGACAAGTTCTTACATAAAGAGTGCTGAAAATCTT-CCTGGGAACCTACATCCT-TGGCTT

-596 CTGF
-CAAATGATCAAATCTCAAATATAGAATTCAGG-GTTTTACA---GGTAGGCATCTTGAGG ATTTCAAATGGT
** **** *   ** * * * **
CCAAA-GATCAATGCCTGTATTTCAGATACAAAAGTTGCACACATAGGAATTCTGGGAGGAGGAGGCATTTCA

-483 CTGF
CCTATAGCCCTCT-----AAAAACGCAAATCATTGCTAAGGGTTGGGGGGAGAAACCTTTTTCGAATTTTTAGG
* ** * * *   **** * *
ACTACAGCCCCCGTAAAGAAAAAAAAAATCCAAAACAAAGAAAAAGAAATATTTTTTTAATTTCTAGG

-368 CTGF
TATGTCAGTGGACAGAACAGGGCAAACTTATTCGAAAAAGAAATAA--GAAATAATTGCCAGTGTGTTTATAA
********** * * **** *   * *** * ** *
TATGTCAGTAGCCAGAACTGGCAAAGAGATTTTTAAGAAGAGATCAGAGAGAATAATCGTTTATTCTAAG

FIG. 1B

```
GA-TGGCCACTCGTCCCTTGTCCCTTGCCTTATATAAAACTCCTACATA    CTGF
 * **         ** ****   *   *     *  * * *  *  *
AACTTATTTTTCTA--GAAAACCATGCCCCAGTAATACCCCCTTGCCCTG   FISP

ACGAGTCTCTTGTTCTCTTCTCTTGTCCCAAAAACCGTTACCTCAAGTGA   CTGF
*   ****  *     **    **   *   ***  *  *** ****** 
TCATATCTTTCAGC-C-ATCAAA----ATGGCCAT---CTCCAGTGA      FISP

TAAAAGCAACT-CACTCCCTTTTCTACTCT-TTGGAGAGTTTCAAGAG     CTGF
 ** *  *** *  ***  ***   *     * *  *   **** ***
AATGGCTATAAGCAC-CCTTCCTCTCAGTAGAAGAACACCAAGAG        FISP

CArGbox
AATTCCTG

```
-251 CTGF
CTATTTGGTGCTGGAAATACTGCGCTTTTTTTTTTTTTT--CTGT-GAGCTGGAGTGTGCCAG    NF-1-like
**    ******    **      *     ***************** ***   ****  ****************
CTTCTTGGTGTGTGCTGGAAACAC-----AGCGCCTTTTTTTTTTTTTCCTGGCGAGCTAAAGTGTGCCAG -134 CTGF
                TIE-like
CGGTGTGAGTTGATGAGGCAGGAAGGTGGGGAGGAATGCCGAGGAATGTCCCTGTTTGTGTAGGACTCCATTCA
*****************    *********** **************  *****************************
CGGTGTGAGTTGATGAGGCAGGAAGGTGGGGAGGAATGTGAGGAATGTCCCTGTTTGTGTAGGACTTCATTCA -15 CTGF
    SP-1        +1
CGGCCGCGCCCCAAACTCACACAACAACTCTTC CTGF
**  * *  ******  *     ******      *****
CGGCCGGCCGGCCT-AGTCTCACACAG---CTCTTC FISP
```

FIG. 1D

```
                                                     TGF-β element
CTTTTTCAGACGGGAGGAATGCTGAGTGTCAAGGGTCAGGATCAAATC   CTGF
*******************         ****************   *  ****************
CTTTTTCAGACGGGAGGAATGTGGAGTGTCAAGGGTCAGGATCAAATC   FISP CATbox              SP-1           TATAbox
GCTCATTGGCGAGCCGCGGGGCGGGCGGAGCCGTATAAAAGCCCTCGGG  CTGF
 *  ***************   ** **   ********************   ***  *
GTTCTTTGGGCGAGCCG--GCTCCCGGGAGCCGTATAAAAGCCCA-GCG  FISP
```

FIG. 1E

```
-823  TCTAGAGCTCGCGGCGAGCTCTAATACGACTCACTATAGGGCGTCGACTCGATCCCTTTT
-763  CTGGAAACATTGATGGCCACTCGTCCCTTGTCCCTATATAAAACTCCTACATATAT
-703  TAAGAGAAAACTAAGCAAGAGTTTTGGAAATCTGCCCCAGGAGACTGCATCCTGAGTCAC
                                                         AP-1
-643  ACGAGTCTTTGTTCTCTTCTTGTCCCAAAACCGTTACCTCAAGTGACAAATGATCAAAT
-583  CTCAAATATAGAATTCAGGGTTTTACAGGTAGGCATCTTGAGGATTTCAAATGGTTAAAA
-523  GCAACTCACTCCTTTTCTACTCTTTGGAGAGTTTCAAGAGCCTATAGCCTCTAAAACGCA
-463  AATCATTGCTAAGGGTTGGGGGGAGAAACCTTTTCGAATTTTTTAGGAATTCCTGCTGT
-403  TTGCCTCTTCAGCTACCTACTTCCTAAAAGGATGTATGTCAGTGGACAGAACAGGGCAA
                              CArG box
-343  ACTTATTCGAAAAAAGAGAATAAGAAATTGCCAGTGTGTTTATAAATGATATGAATCAG
                                                         AP-1
-283  GAGTGGTGCGAAGAGGATAGGAGAAAAAAATTCTATTTGGTGCTGGAAATACTGCGCTTT
-223  TTTTTTCCTTTTTTTTTTTTCTGTGAGCTGGAGTGCCAGCTTTTTCAGACGGAGGAA
                                     NF-1 like
-163  TGCTGAGTGTCAAGGGGTCAGGATCAATCCGGTGTGAGTTGATGAGGCAGGAAGGTGGGG
                                         TIE-like
-103  AGGAATGCGAGGAATGTCCCGTGTTTGTGTAGGACTCCATTCAGCTCATTGGCGAGCCGCG
                                                         CATbox
-43   GCCGCCCGGGAGCGTATAAAAGCCCTGCGGCCCCCAAACTCACACAACAACTCTTC
      SP-1          TATAbox                      +1
 17   CCCGCTGAGAGGAGACAGCCAGTGCGACTCCACCCTCCAGCTCGACGGCAGCCCGCCCCGG
```

FIG. 1F

```
 77  CCGACAGCCCCGAGACGACAGCCCCGGCGGCGTCCCCACCTCCGACCACCGCCAGC
137  GCTCCAGGCCCCGGCCTCCGCTCCCCGCACCGCGCTCCGCGCTCCGCCAGTGCC
197  AACCATGACCGCCGCCAGTATGGGCCCCGTCCGCGCCTTCGTGGTCCTCCTCGCCCT
       M  T  A  A  S  M  G  P  V  R  V  A  F  V  V  L  L  A
257  CTGCAGCCGGGGTAAGC......Intron 1.............GCTGCCAGGGAGGGACTC
       L  C  S  R  .........................   
317  GGGGCCGGCCGGCCGGTGCGCGGGCCGACCGAGCGCCCGACCCTGTCCTCCCT
378  GCAGCCGGCCGTCGGCCAGAACTGCAGCGGGCCCTGCCGCGAGCCGGGCCC
       P  A  V  G  Q  N  C  S  G  P  C  R  C  P  D  E  P  A
437  GCGCTGCCCGGGCCGGGCGTGAGCCTCGTGCTGGACGGCTGCTGCCGGTCTGCGC
       P  R  C  P  A  G  V  S  L  V  L  D  G  C  C  R  V  C
497  CAAGCAGCTGGGCGAGCTGTGCACCGAGCGCGACCCCTGCGACCCACAAGGCCCTCTT
       A  K  Q  L  G  E  L  C  T  E  R  D  P  C  D  P  H  K  G  L
557  CTGTGACTTCGGCTCCCCGGCCAACCGCAAGATCGGCGTGTGCACCGGTAAGACCCGCAG
       F  C  D  F  G  S  P  A  N  R  K  I  G  V  C  T  ...Intron 2..
```

FIG. 1G

```
 617  CCCCCACCGCTAGGTGTCCGGCCGCCTCCTCACGCCCACCCGCCCGCTGGAAAAAG
 677  AAACCGCTCGGACTGAGTTTCTCTTCCAGCTGCCAGCCCCTGCCAGCCCAGA
 737  TCCCAACTCGCATCCCTGCTTCCCTCTTCCTCTTCCAGCTGAGAGTGCCCCAATGCCTGACTCTGCAT
 797  CCCCCACCCCTCCTCCTCTTCCCTCTTCCAGCCAAAGATGGTGCTCCCTGCATCTTCG
              . . . . . . .  A   K   D   G   A   P   C   I   F
 857  GTGGTACGGTGTACCGCAGCGGAGAGTCCTTCCAGAGCAGTGCAGTACCAGTGCACGT
       G   G   T   V   Y   R   S   G   E   S   F   Q   S   C   K   Y   Q   C   T
 917  GCCTGGACGGCGGTGGGCCTGCATGGCAGCATGGACGTTCGTGCCCAGCC
       C   L   D   G   A   V   G   C   M   P   L   C   S   M   D   V   R   L   P   S
 977  CTGACTGCCCCTTCCCCGAGGAGGGTCAAGCTGGGAAATGCTGCGAGGAGTGGGGTGT
       P   D   C   P   F   P   R   R   V   K   L   P   G   K   C   C   E   E   W   V
1037  GTGACGAGCCCAAGGACCCAAACCGTGGTTGGGCCCTGCCCCTCGCGGGGTGAGTCGAGTCTTC
       C   D   E   P   K   D   Q   T   V   V   G   P   A   L   A  . . . . . . . . .
1097  CTCTAAGTCAGGTCGTGATTCTCTCCCAGGGAGGGAGTCCTAACTGTGCCGACGAACG
                                                              . . . . . . A   Y
1157  GGGAAATACCTTATCAGGCGTTTATCAGGCGTTTGTGTCTCGCAGCTTACC
1217  GACTGGAAGACACGTTTGGCCCAGACCCAACTATGATTAGAGCCAACTGCCTGGTCCAGA
       R   L   E   D   T   F   G   P   D   P   T   M   I   R   A   N   C   L   V   Q
1277  CCACAGAGTGGAGCGCCTTCCCAAGACCTGTGGATGGGCATCTCCACCGGGTTACCA
       P   Q   S   G   E   A   S   K   T   C   G   M   G   I   S   T   R   V   T
1337  ATGACAACGCCCTCCTGCAGGCTAGAAGCAGAGCCGCCTGTGCATGGTCAGGCCTTGCG
       M   T   T   P   L   Q   A   R   S   R   A   A   C   M   V   R   P   C
1397  AAGCTGACCTGAAGAGAACATTAAGGTACATGTTCTGCTCCTATTAACTATTTTTCACA
       N   D   N   A   S   C   R   L   E   K   Q   S   R   L   C   M   V   R   P   C
1457  GGAAAAACAGTGGATAGGACCCAACTTAGGGCTCTTGCACGCTTGTGTTAGTATAAGCCCGT
       E   A   D   L   E   N   I   K  . . . . . . . . . Intron 4 . . . . . . . . .
1517  TATCTCCAAAACTATCTCCACTAGCTGAGCTGTTTTGCTGGAATGAGAGCTTGTGTAATAGC
1577  AACCACCAGTTTTCCACTACGAAATCTTCCACAGGGTTAGTTAATTCAAGACATTCCAAG
1637  AGAGGCTCTGGCTATTTTTGGACATAGCAAATCAAACTTCCTCCCCTCAAAATA
1697  TAAACAGAAGTCAGACAACAGAGACTAAAACCACAGAGGGTTGAAGAAAGCCACTCCTCT
```

```
2897  ATTCTGCTCAGATAGAATGACACAGTCCGTCAAAACAGATTGTTTGCAAAGGGGAGGCATCA
2957  GTGTCTTGGCAGGCTGATTTCTAGGTAGGAAATGTGGTAGCTCACGTTTAATGAACAAAT
3017  GGCCTTATAAAAACTGAGTGACTCCTATATAGCTCAGTTTTTCACCTGAAGCATTTG
3077  TTTCTACTTTGATATGACTGTTTTCGACAGTTTATTGTTGAGAGTGTGACCAAAAGTT
3137  ACATGTTTGCACCTTTCTAGTTGAAAATAAAGTGTATATTTTTCTATAAAGGGCTTGGT
3197  TATTCATTTATCCTTCTAAACATTTCTGAGTTTTTCTAAATATCTTTAATTATTCTATACATTAAT
3257  TAATCATAAGATAATTCACCAATAATTTTCTAAATATCTTTAATTATTCTATACATTAAT
3317  AAATTGATTATTCCATAGAATTTTTATGTAAACATACTTCCACACTGAATCAAGTATCACA
3377  GACTTGCAGGCATA
```

*FIG. 1J*

# METHODS OF IDENTIFYING A COMPOSITION THAT ALTERS CONNECTIVE TISSUE GROWTH FACTOR EXPRESSION

This is a divisional of U.S. patent application Ser. No. 08/459,717, filed Jun. 2, 1995, now issued as U.S. Pat. No. 5,770,207, which is a continuation-in-part application of Ser. No. 08/386,680, filed Feb. 10, 1995, now issued as U.S. Pat. No. 5,585,270, which is a divisional of Ser. No. 08/167,628, filed on Dec. 14, 1993, now issued as U.S. Pat. No. 5,408,040, which is a continuation of Ser. No. 07/752,427, filed Aug. 30, 1991, now abandoned.

This invention was made with Government support by grant no. GM 37223, awarded by the National Institutes of Health. The Government has certain rights in this invention.

BACKGROUND OF THE INVENTION

1. Field of the Invention

This invention relates generally to the field of growth factors and specifically to Connective Tissue Growth Factor (CTGF), a polynucleotide encoding this factor and methods of use for CTGF.

2. Related Art

Growth factors are a class of secreted polypeptides that stimulate target cells to proliferate, differentiate and organize in developing tissues. The action of growth factors is dependent on their binding to specific receptors which stimulates a signalling event within the cell. Examples of some well-studied growth factors include platelet-derived growth factor (PDGF), insulin-like growth factor (IGF-I), transforming growth factor beta (TGF-β), transforming growth factor alpha (TGF-α), epidermal growth factor (EGF), and fibroblast growth factor (FGF).

PDGF is a cationic, heat-stable protein found in the alpha-granules of circulating platelets and is known to be a mitogen and a chemotactic agent for connective tissue cells such as fibroblasts and smooth muscle cells. Because of the activities of this molecule, PDGF is believed to be a major factor involved in the normal healing of wounds and pathologically contributing to such diseases as atherosclerosis and fibrotic diseases. PDGF is a dimeric molecule consisting of an A chain and a B chain. The chains form heterodimers or homodimers and all combinations isolated to date are biologically active.

Studies on the role of various growth factors in tissue regeneration and repair have led to the discovery of PDGF-like proteins. These proteins share both immunological and biological activities with PDGF and can be blocked with antibodies specific to PDGF.

These new growth factors may play a significant role in the normal development, growth, and repair of human tissue. Therapeutic agents derived from these molecules may be useful in augmenting normal or impaired growth processes involving connective tissues in certain clinical states, e.g., wound healing. When these growth factors are involved pathologically in diseases, therapeutic developments from these proteins may be used to control or ameliorate uncontrolled tissue growth.

The formation of new and regenerating tissue requires the coordinate regulation of various genes that produce both regulatory and structural molecules which participate in the process of cell growth and tissue organization. Transforming growth factor beta (TGF-β) appears to be a central regulatory component of this process. TGF-β is released by platelets, macrophages and neutrophils which are present in the initial phases of the repair process. TGF-β can act as a growth stimulatory factor for mesenchymal cells and as a growth inhibitory factor for endothelial and epithelial cells. The growth stimulatory action of TGF-β appears to be mediated via an indirect mechanism involving autocrine growth factors such as PDGF BB or PDGF AA or connective tissue growth factor (CTGF).

Several members of the TGF-β superfamily possess activities suggesting possible applications for the treatment of cell proliferative disorders, such as cancer. In particular, TGF-β has been shown to be potent growth inhibitor for a variety of cell types (Massague, Cell 49:437, 1987), MIS has been shown to inhibit the growth of human endometrial carcinoma tumors in nude mice (Donahoe, et al., Ann. Surg. 194:472, 1981), and inhibin α has been shown to suppress the development of tumors both in the ovary and in the testis (Matzuk, et al., Nature, 360:313, 1992).

Many of the members of the TGF-β family are also important mediators of tissue repair. TGF-β has been shown to have marked effects on the formation of collagen and causes of striking angiogenic response in the newborn mouse (Roberts, et al., Proc. Natl. Acad. Sci., USA 83:4167, 1986). The bone morphogenic proteins (BMPs) can induce new bone growth and are effective for the treatment of fractures and other skeletal defects (Glowacki, et al., Lancet, 1:959, 1981; Ferguson, et al., Clin. Orthoped. Relat. Res., 227:265, 1988; Johnson, et al., Clin Orthoped. Relat. Res., 230:257, 1988).

The isolation of growth factors and the genes encoding them is important in the development of diagnostics and therapeutics for various connective tissue-related disorders. The present invention provides such an invention.

SUMMARY OF THE INVENTION

Various cell types produce and secrete PDGF and PDGF-related molecules. In an attempt to identify the type of PDGF dimers present in the growth media of cultured endothelial cells, a new growth factor was discovered. This previously unknown factor, termed Connective Tissue Growth Factor (CTGF), is related immunologically and biologically to PDGF, however it is the product of a distinct gene.

In a first aspect, the present invention provides a polypeptide growth factor for connective tissue cells. The polypeptide is a mitogenic agent and a chemotactic agent for cells.

In a second aspect, the present invention provides a polynucleotide encoding a connective tissue growth factor characterized as encoding a protein (1) existing as a monomer of approximately 36–38 kD molecular weight, and (2) capable of binding to a PDGF receptor.

In a further aspect, the invention provides a method for accelerating wound healing in a subject by applying to the wound an effective amount of a composition which contains CTGF.

In yet another aspect, the invention provides a method of diagnosing pathological states in a subject suspected of having pathology characterized by a cell proliferative disorder which comprises, (1) obtaining a sample suspected of containing CTGF from the subject, (2) determining the level of CTGF in the sample, and (3) comparing the level of CTGF in the sample to the level of CTGF in normal tissues.

A method of ameliorating diseases characterized by a cell proliferative disorder, by treating the site of the disease with an effective amount of a CTGF reactive agent is also provided.

The present invention identifies a TGF-β responsive or regulatory element in the 5' untranslated nucleotides of the CTGF gene (about −157 to −145). Based on the identification of this element, the invention now provides a method for identifying a composition which affects CTGF expression comprising incubating components comprising the composition and TGF-β regulatory element (TβRE), in the presence of a TGF-β factor which regulates TβRE, and measuring the effect of the composition on CTGF expression. Thus, the invention provides a means for drug discovery for treatment of fibrotic diseases.

BRIEF DESCRIPTION OF THE DRAWINGS

FIGS. 1B through 1E show a comparison of nucleotide sequences between CTGF promoter (nucleotides 1 to 840; SEQ ID NO: 1) and fisp-12 promoter (SEQ ID NO: 9). Identical nucleotides are marked with asterisks. The TATA box and other consensus sequences are indicated and shaded. The site of transcriptional initiation is indicated at position number +1.

FIGS. 1C through 1J show the complete nucleotide (SEQ ID NO: 1) and deduced amino acid (SEQ ID NO: 2) sequence for the CTGF structural gene and 5' and 3' untranslated sequences.

FIG. 5 panel A shows a sequence analysis of the region from −205 to −109. Sequence from −200 to −113 is shown. Lane G is the G sequence of the intact labeled probe, Lane S is the sequence of the shifted band and Lane F is the sequence of the non-shifted free probe from the same sample. The only region containing mission G residues is from positions −157 to −145.

DETAILED DESCRIPTION OF THE INVENTION

Figures 1A, 7:
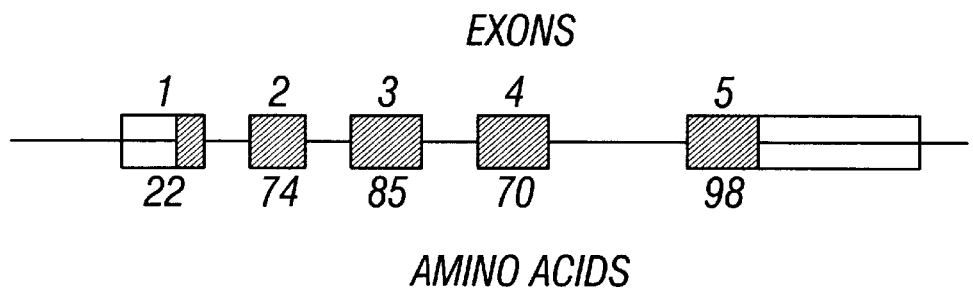
FIG. 1A shows the structural organization of the CTGF gene. Exons are indicated by boxed regions, with solid areas in the gene corresponding to the open reading frame.
FIG. 7 shows point mutations in the TβRE decreases induction of the CTGF promoter by TGF-β.

The present invention discloses a novel protein growth factor called Connective Tissue Growth Factor (CTGF).

This protein may play a significant role in the normal development, growth and repair of human tissue. The discovery of the CTGF protein and cloning of the cDNA encoding this molecule is significant in that it is a previously unknown growth factor having mitogenic and chemotactic activities for connective tissue cells. The biological activity of CTGF is similar to that of PDGF, however, CTGF is the product of a gene unrelated to the A or B chain genes of PDGF. Since CTGF is produced by endothelial and fibroblastic cells, both of which are present at the site of a wound, it is probable that CTGF functions as a growth factor in wound healing.

Pathologically, CTGF may be involved in diseases in which there is an overgrowth of connective tissue cells, such as cancer, tumor formation and growth, fibrotic diseases (e.g., pulmonary fibrosis, kidney fibrosis, glaucoma) and atherosclerosis. The CTGF polypeptide is useful as a therapeutic in cases in which there is impaired healing of skin wounds or there is a need to augment the normal healing mechanisms. Additionally, antibodies to CTGF polypeptide or fragments could be valuable as diagnostic tools to aid in the detection of diseases in which CTGF is a pathological factor. Therapeutically, antibodies or fragments of the antibody molecule could also be used to neutralize the biological activity of CTGF in diseases where CTGF is inducing the overgrowth of tissue.

The primary biological activity of CTGF polypeptide is its mitogenicity, or ability to stimulate target cells to proliferate. The ultimate result of this mitogenic activity in vivo, is the growth of targeted tissue. CTGF also possesses chemotactic activity, which is the chemically induced movement of cells as a result of interaction with particular molecules. Preferably, the CTGF of this invention is mitogenic and chemotactic for connective tissue cells, however, other cell types may be responsive to CTGF polypeptide as well.

The CTGF polypeptide of the invention is characterized by existing as a monomer of approximately 36–38 kD molecular weight. CTGF is secreted by cells and is active upon interaction with a receptor on a responsive cell. CTGF is antigenically related to PDGF although there is little if any peptide sequence homology. Anti-PDGF antibody has high affinity to the non-reduced forms of the PDGF isomers and the CTGF molecule and ten-fold less affinity to the reduced forms of these peptides, which lack biological activity. This suggests that there are regions of shared tertiary structure between the PDGF isomers and the CTGF molecule, resulting in common antigenic epitopes.

The term "substantially pure" as used herein refers to CTGF which is substantially free of other proteins, lipids, carbohydrates or other materials with which it is naturally associated. The substantially pure polypeptide will yield a single major band on a non-reducing polyacrylamide gel. The purity of the CTGF polypeptide can also be determined by amino-terminal amino acid sequence analysis. CTGF polypeptide includes functional fragments of the polypeptide, so long as the mitogenic and chemotactic activities of CTGF are retained. Smaller peptides containing the biological activity of CTGF are included in the invention. Additionally, more effective CTGF molecules produced, for example, through site directed mutagenesis of the CTGF cDNA are included.

The invention provides an isolated polynucleotide encoding the CTGF protein. The term "isolated" as used herein refers to a polynucleotide which is substantially free of other polynucleotides, proteins, lipids, carbohydrates or other materials with which it is naturally associated. These polynucleotides include DNA, cDNA and RNA sequences which encode connective tissue growth factor. It is understood that all polynucleotides encoding all or a portion of CTGF are also included herein, so long as they encode a polypeptide with the mitogenic and chemotactic activity of CTGF. Such polynucleotides include naturally occurring forms, such as allelic variants, and intentionally manipulated forms, for example, mutagenized polynucleotides, as well as artificially synthesized polynucleotides. For example, CTGF polynucleotide may be subjected to site-directed mutagenesis. The polynucleotides of the invention include sequences that are degenerate as a result of the genetic code. There are only 20 natural amino acids, most of which are specified by more than one codon. Therefore as long as the amino acid sequence of CTGF is functionally unchanged, all degenerate nucleotide sequences are included in the invention.

The term "polynucleotide" also denotes DNA, cDNA and RNA which encode untranslated sequences which flank the structural gene encoding CTGF. For example, a polynucleotide of the invention includes 5' regulatory nucleotide sequences and 3' untranslated sequences associated with the CTGF structural gene. The polynucleotide of the invention which includes the 5' and 3' untranslated region is illustrated in FIG. 1C. The 5' regulatory region, including the promoter, is illustrated in FIG. 1B.

The sequence of the cDNA for CTGF contains an open reading frame of 1047 nucleotides with an initiation site at position 130 and a TGA termination site at position 1177 and encodes a peptide of 349 amino acids. There is only a 40% sequence homology between the CTGF cDNA and the cDNA for both the A and B chains of PDGF.

The present invention provides CTGF promoter nucleotides −823 to +74 (nucleotides 1 to 897; SEQ ID NO: 1) as well as a TGF-β regulatory element (TβRE) located between positions −162 and −128 (nucleotides 664 to 698; SEQ ID NO: 1) of the CTGF promoter sequence. Methylation interference and competition gel shift assays map a unique 13-nucleotide sequence between positions −157 and −145 (nucleotides 669 to 681; SEQ ID NO. 1) delineating a novel TGF-β cis-regulatory element.

The CTGF open reading frame encodes a polypeptide which contains 39 cysteine residues, indicating a protein with multiple intramolecular disulfide bonds. The amino terminus of the peptide contains a hydrophobic signal sequence indicative of a secreted protein and there are two N-linked glycosylation sites at asparagine residues 28 and 225 in the amino acid sequence. CTGF is a member of a protein family that includes serum induced immediate early gene products such as Cyr61 (O'Brien, et al., *Mol. Cell. Biol.*, 10:3569, 1990) and Fisp12 (Ryseck, et al., *Cell Growth & Differentiation*, 2:225, 1991)/BigM2 (Brunner, et al., *DNA and Cell Biol.*, 10:293, 1991); a v-src induced peptide (CEF-10) (Simmons, et al., *Proc. Natl. Acad. Sci., USA*, 86:1178, 1989) and a putative oncoprotein (nov) (Joliot, et al., *Mol. Cell Biol*, 12:10, 1992). Twisted gastrulation (tsg), a gene that functions to control the induction of medial mesodermal elements in the dorsal/ventral patterning of Drosophila embryogenesis is more distantly related to CTGF (Mason, et al., *Genes and Devel*, 8:1489, 1994). There is a 45% overall sequence homology between the CTGF polypeptide and the polypeptide encoded by the CEF-10 mRNA transcript (Simmons, et al., *Proc. Natl. Acad. Sci. USA* 86:1178, 1989); the homology reaches 52% when a putative alternative splicing region is deleted.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences and 2) antibody screening of expression libraries to detect shared structural features.

Screening procedures which rely on nucleic acid hybridization make it possible to isolate any gene sequence from any organism, provided the appropriate probe is available. For example, oligonucleotide probes, which correspond to a part of the sequence encoding the protein in question, can be synthesized chemically. This requires that short, oligopeptide, stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research,* 9:879, 1981).

A cDNA expression library, such as lambda gt11, can be screened indirectly for CTGF peptides having at least one epitope, using antibodies specific for CTGF or antibodies to PDGF which cross react with CTGF. Such antibodies can be either polyclonally or monoclonally derived and used to detect expression product indicative of the presence of CTGF cDNA.

DNA sequences encoding CTGF can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used.

DNA sequences encoding CTGF can be expressed in vivo in either prokaryotes or eukaryotes. Methods of expressing DNA sequences having eukaryotic coding sequences in prokaryotes are well known in the art. Hosts include microbial, yeast and mammalian organisms.

Biologically functional viral and plasmid DNA vectors capable of expression and replication in a host are known in the art. Such vectors are used to incorporate DNA sequences of the invention. In general, expression vectors containing promotor sequences which facilitate the efficient transcription of the inserted eukaryotic genetic sequence are used in connection with the host. The expression vector typically contains an origin of replication, a promoter, and a terminator, as well as specific genes which are capable of providing phenotypic selection of the transformed cells.

In addition to expression vectors known in the art such as bacterial, yeast and mammalian expression systems, baculovirus vectors may also be used. One advantage to expression of foreign genes in this invertebrate virus expression vector is that it is capable of expression of high levels of recombinant proteins, which are antigenically and functionally similar to their natural counterparts. Baculovirus vectors and the appropriate insect host cells used in conjunction with the vectors will be known to those skilled in the art.

The term "recombinant expression vector" refers to a plasmid, virus or other vehicle known in the art that has been manipulated by insertion or incorporation of the CTGF genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

The isolation and purification of host cell expressed polypeptides of the invention may be by any conventional means such as, for example, preparative chromatographic separations and immunological separations such as those involving the use of monoclonal or polyclonal antibody.

Transformation of the host cell with the recombinant DNA may be carried out by conventional techniques well known to those skilled in the art. Where the host is prokaryotic, such as *E. coli,* competent cells which are capable of DNA uptake can be prepared from cells harvested after exponential growth and subsequently treated by the CaCl$_2$ method using procedures well known in the art. Alternatively, MgCl$_2$ or RbCl could be used.

Where the host used is a eukaryote, various methods of DNA transfer can be used. These include transfection of DNA by calcium phosphate-precipitates, conventional mechanical procedures such as microinjection, insertion of a plasmid encased in liposomes, or the use of virus vectors. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors,* Cold Spring Harbor Laboratory, Gluzman ed., 1982). Examples of mammalian host cells include COS, BHK, 293, and CHO cells.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., *Nature,* 340:205, 1989; Rose, M. et al., *Gene,* 60:237, 1987).

The invention provides antibodies which are specifically reactive with CTGF polypeptide or fragments thereof. Although this polypeptide is cross reactive with antibodies to PDGF, not all antibodies to CTGF will also be reactive with PDGF. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256:495, 1975; *Current Protocols in Molecular Biology,* Ausubel, et al., ed., 1989). Monoclonal antibodies specific for CTGF can be selected, for example, by screening for hybridoma culture supernatants which react with CTGF, but do not react with PDGF.

Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature,* 256:495, 1975; *Current Protocols in Molecular Biology,* Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual,* Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to CTGF polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology,* Wiley Interscience, 1994, incorporated herein by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The invention provides a method for accelerating wound healing in a subject, e.g., a human, by applying to the wound an effective amount of a composition which contains CTGF, preferably purified. PDGF and PDGF-related molecules, such as CTGF, are involved in normal healing of skin wounds. The CTGF polypeptide of this invention is valuable as a therapeutic in cases in which there is impaired healing of skin wounds or there is a need to augment the normal healing mechanisms, e.g., burns. One important advantage to using CTGF protein to accelerate wound healing is attributable to the molecule's high percentage of cysteine residues. CTGF, or functional fragments thereof, is more stable and less susceptible to protease degradation than PDGF and other growth factors known to be involved in wound healing.

CTGF is produced by endothelial cells and fibroblastic cells, both of which are present at the site of a skin wound. Therefore, agents which stimulate the production of CTGF can be added to a composition which is used to accelerate wound healing. Preferably, the agent of this invention is transforming growth factor beta (TGF-β), however, it is likely that other TGF-β family members will also be useful in accelerating wound healing by inducing CTGF. The composition of the invention aids in healing the wound, in part, by promoting the growth of connective tissue. The composition is prepared by combining, in a pharmaceutically acceptable carrier substance, e.g., inert gels or liquids, the purified CTGF and TGF-β.

The term "cell proliferative disorder" refers to pathological states characterized by the continual multiplication of cells resulting in an overgrowth of a cell population within a tissue. The cell populations are not necessarily transformed, tumorigenic or malignant cells, but can include normal cells as well. For example, CTGF may be involved pathologically by inducing a proliferative lesion in the intimal layer of an arterial wall, resulting in atherosclerosis. Instead of trying to reduce risk factors for the disease, e.g., lowering blood pressure or reducing elevated cholesterol levels in a subject, CTGF inhibitors or antagonists of the invention would be useful in interfering with the in vivo activity of CTGF associated with atherosclerosis. CTGF antagonists are useful in treating other disorders associated with overgrowth of connective tissues, such as various fibrotic diseases, including scleroderna, arthritis, alcoholic liver cirrhosis, keloid, and hypertropic scar.

The present invention provides a method to detect the presence of elevated levels of CTGF to be used diagnostically to determine the presence of pathologies characterized by a cell proliferative disorder. For example, a sample suspected of containing CTGF is obtained from a subject, the level of CTGF determined and this level is compared with the level of CTGF in normal tissue. The level of CTGF can be determined by immunoassays using anti-CTGF antibodies, for example. Other variations of such assays which are well known to those skilled in the art, such as radioimmunoassay (RIA), ELISA and immunofluorescence can also be used to determine CTGF levels in a sample. Alternatively, nucleic acid probes can be used to detect and quantitate CTGF mRNA for the same purpose.

The invention also discloses a method for ameliorating diseases characterized by a cell proliferative disorder by treating the site of the disease with an effective amount of a CTGF reactive agent. The term "ameliorate" denotes a lessening of the detrimental effect of the disease-inducing response in the patient receiving therapy. Where the disease is due to an overgrowth of cells, an antagonist of CTGF polypeptide is effective in decreasing the amount of growth factor that can bind to a CTGF specific receptor on a cell. Such an antagonist may be a CTGF specific antibody or functional fragments thereof (e.g., Fab, F(ab')$_2$). Alternatively, a polynucleotide containing the TβRE region of the promoter may be used as a CTGF reactive agent by acting as a competitor for TGF-β. The treatment requires contacting the site of the disease with the antagonist. Where the cell proliferative disorder is due to a diminished amount of growth of cells, a CTGF reactive agent which is stimulatory is contacted with the site of the disease. For example, TGF-β is one such reactive agent. Other agents will be known to those skilled in the art.

When a cell proliferative disorder is associated with the expression of CTGF, a therapeutic approach which directly interferes with the translation of CTGF messages into protein is possible. For example, antisense nucleic acid or ribozymes could be used to bind to the CTGF mRNA or to cleave it. Antisense RNA or DNA molecules bind specifically with a targeted gene's RNA message, interrupting the expression of that gene's protein product. The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. These and other uses of antisense methods to inhibit the in vitro translation of genes are well known in the art (Marcus-Sakura, *Anal., Biochem.,* 172:289, 1988).

Antisense nucleic acids are DNA or RNA molecules that are complementary to at least a portion of a specific mRNA molecule (Weintraub, *Scientific American,* 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target CTGF producing cell. The use of antisense methods to inhibit the in vitro translation of genes is well known in the art (Marcus-Sakura, *Anal.Biochem.,* 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.,* 1(3):227, 1991; Helene, C., *Anticancer Drug Design,* 6(6):569, 1991) for example, the TβRE region of the CTGF promoter.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J.Amer.Med. Assn.,* 260:3030, 1988). A major advantage of this approach is that, because they are sequence-specific, only mRNAs with particular sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The identification of the promoter element of the CTGF gene and specifically, the TGF-β responsive/regulatory element (TβRE) (5'-GTGTCAAGGGGTC-3' (SEQ ID NO:8); nucleotides −157 and −145), provides a source for a screening method for identifying compounds or compositions which affect the expression of CTGF. Thus, in another embodiment, the invention provides a method for identifying a composition which affects CTGF expression comprising incubating components comprising the composition and a TGF-β responsive element of the CTGF promoter, wherein the incubating is carried out under conditions sufficient to allow the components to interact; and measuring the effect of the composition on CTGF expression. The method further comprises adding TGF-β, or a TGF-β family member reactive with the TβRE, to the reaction mixture. Therefore, the method allows identification of TGF-β inhibitors, or anti-fibrotic compounds. Preferably, the promoter region used in the screening assays described herein includes nucleotides −823 to +74, however, smaller regions that include the TGF-β responsive element would also be useful in the method of the invention (e.g., −162 to −128 or −157 to −145).

The observed effect on CTGF expression may be either inhibitory or stimulatory. For example, the increase or decrease of CTGF activity can be measured by a biological assay for CTGF, as described in the examples herein (e.g., EXAMPLES 1 and 2). Alternatively, a polynucleotide encoding both the regulatory (promoter) and structural region of CTGF may be inserted into an expression vector and the effect of a composition on transcription of CTGF can be measured, for example, by Northern blot analysis. A radioactive compound is added to the mixture of components, such as $^{32}$P-ATP, and radioactive incorporation into CTGF mRNA is measured.

Alternatively, a composition which affects the expression of CTGF can be identified by operably linking a reporter gene with the TGF-β responsive region of the promoter of CTGF, incubating the components including the composition being tested, the reporter gene construct and TGF-β and assaying for expression of the reporter gene. Such reporter genes will be known to those of skill in the art, and include but are not limited to a luciferase gene, chloramphenicol acetyl transferase gene (CAT assay) or β-galactosidase gene.

The inducer of the TβRE can be added prior to or following the addition of the composition to be tested. Preferably, it is added after the composition is added. An inducer of this region in the CTGF promoter is preferably TGF-β, however, it is likely that other members of the TGF-β family will also be useful for induction from this element. Other such family members or factors will be known to those of skill in the art.

The method of the invention is preferably performed in an indicator cell. An "indicator cell" is one in which activation of CTGF or the reporter gene can be detected. Examples of mammalian host indicator cells include the pre-B cell line, 70Z/3, Jurkat T, COS, BHK, 293, CHO, HepG2, and HeLa cells. Other cell lines can be utilized as indicator cells, as long as the level of reporter gene can be detected. The cells can be recombinantly modified to contain an expression vector which encodes one or more additional copies of the TβRE binding motif, preferably operatively linked to a reporter gene. The cells can also be modified to express CTGF, as described above.

The reporter gene is a phenotypically identifiable marker for detection of stimulation or inhibition of CTGF activation. Markers preferably used in the present invention include the LUC gene whose expression is detectable by a luciferase assay. Examples of markers typically used in prokaryotic expression vectors include antibiotic resistance genes for ampicillin (β-lactamases), tetracycline and chloramphenicol (chloramphenicol acetyl-transferase). Examples of such markers typically used in mammalian expression vectors, which are preferable for the present invention, include the gene for adenosine deaminase (ADA), aminoglycoside phosphotransferase (neo, G418), dihydrofolate reductase (DHFR), hygromycin-B-phosphotransferase (HPH), thymidine kinase (TK), xanthine guanine phosphoribosyltransferse (XGPRT, gpt) and β-galactosidase (β-gal).

In yet another embodiment, the invention provides a method of treating a subject having a cell proliferative disorder associated with CTGF gene expression in a subject, comprising administering to a subject having the disorder a therapeutically effective amount of an agent which modulates CTGF gene expression, thereby treating the disorder. The term "modulate" refers to inhibition or suppression of CTGF expression when CTGF is overexpressed, and induction of expression when CTGF is underexpressed. The term "therapeutically effective" means that amount of CTGF agent which is effective in reducing the symptoms of the CTGF associated cell proliferative disorder.

The agent which modulates CTGF gene expression may be a polynucleotide for example. The polynucleotide may be an antisense, a triplex agent, or a ribozyme, as described above. For example, an antisense may be directed to the structural gene region or to the promoter region of CTGF.

The agent also includes a polynucleotide which includes the TβRE of the invention. Preferably this region corresponds to nucleotides −162 to −128 of the CTGF regulatory polypeptide illustrated in FIG. 1B. More specifically, the TβRE region corresponds to about −157 to −145 in FIG. 1B. These polynucleotides are useful as competitive inhibitors or pseudosubstrates for TGF-β or other growth factors which bind to the TβRE and induce CTGF transcription.

Delivery of antisense, triplex agents, ribozymes, achieved using a recom and the like can be achieved using a recombinant expression vector such as a chimeric virus or a colloidal dispersion system. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for antisense polynucleotides a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The agent which modulates CTGF gene expression in the method of the invention includes agents which cause an elevation in cyclic nuclotides in the cell. For example, agents such as cholera toxin or 8Br-cAMP are preferably administered to a subject having a cell proliferative disorder associated with CTGF gene expression. Preferably, the cyclic nucleotide that is elevated after treatment in the method of the invention is cAMP or a cAMP analog, either functional or structural, or both. Those of skill in the art will know of other agents which induce cAMP or similar analogs in a cell and which are useful in the method of the invention.

The therapeutic agents useful in the method of the invention can be administered parenterally by injection or by gradual perfusion over time. Administration may be intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also includes a pharmaceutical composition comprising a therapeutically effective amount of CTGF in a pharmaceutically acceptable carrier. Such carriers include those listed above with reference to parenteral administration.

The present Examples (see EXAMPLE 10), demonstrate that TGF-β induction of CTGF is cell type specific (e.g., fibroblast). Consequently, the CTGF promoter region, including the TβRE, is useful for the expression of a structural gene specifically in connective tissue cells. It is envisioned that any gene product of interest can be specifically produced in a connective tissue cell, once operably linked to the TβRE, and in the presence of TGF-β. For example, it may be desirable to operably link PDGF or another growth factor to a polynucleotide containing TβRE, thereby specifically producing PDGF or another factor in a connective tissue cell. Alternatively, in cases where the level of CTGF or other factor produced is elevated, it may be desirable to introduce an antisense for CTGF, for example, under control of TβRE, thereby decreasing the production of CTGF in the cell.

The following examples are intended to illustrate but not limit the invention. While they are typical of those that might be used, other procedures known to those skilled in the art may alternatively be used.

EXAMPLE 1

Identification and Partial Purification of Mitogen from HUVE Cells PDGF-Immunorelated Cells Human umbilical vein endothelial (HUVE) cells were isolated from fresh human umbilical cords by collagenase perfusion (Jaffe, et al., *Human Pathol.,* 18:234, 1987) and maintained in medium 199 with 20% FCS, 0.68 mM L-glutamine, 20 μg/ml Gentamicin, 90 μg/ml porcine heparin (Sigma, St. Louis, Mo.), and 50 μg/ml Endothelial Cell Growth Supplement (Sigma). Cells used for media collection were third passage cells. Cells were identified as endothelial cells by their non-overlapping cobblestone morphology and by positive staining for Factor-VIII related antigen. NRK cells were obtained from American Type Culture, NIH/3T3 cells were a gift from S. Aaronson (NCI; Bethesda, Md.), and both cell lines were maintained in DMEM, 10% FCS, 20 μg/ml Gentamicin. Fetal bovine aortic smooth muscle cells were obtained from tissue explants as previously described (Grotendorst, et al., *Proc. Natl. Acad. Sci. USA,* 78 :3669, 1981) and maintained in DMEM, 10% FCS, 20 μg/ml Gentamicin, and used in assays at second or third passage.

Growth Factors and Antibodies

Human PDGF was purified to homogeneity from platelets as described previously (Grotendorst, *Cell,* 36:279, 1984). Recombinant AA, BB, and AB chain dimeric PDGF molecules were obtained from Creative Biomolecules, (Hopkinton, Mass.). FGF was obtained from Sigma. Purified PDGF or synthetic peptides containing the amino and carboxyl sequences of the mature PDGF A and B chain molecules were used to raise antibodies in goats. Goats were immunized with 20 µg of purified PDGF or 50 µg of synthetic peptide in Freunds complete adjuvant by multiple intradermal injections. Immune sera were collected seven days after the fourth rechallenge (in Freunds incomplete adjuvant) and subsequent rechallenges. The anti-PDGF antibody did not show any cross-reactivity to TGF-β, EGF, or FGF in immunoblot analysis. The anti-peptide antibodies were sequence specific and did not cross-react with other synthetic peptide sequences or with recombinant PDGF peptides which did not contain the specific antigenic sequence. This was determined by Western blot and dot blot analysis.

Antibody Affinity Column

Goat anti-human PDGF IgG (150 mg) was covalently bound to 25 mls of Affi-Gel 10 support (BioRad) according to the manufacturers instructions with a final concentration of 6 mg IgG/ml gel. The column was incubated with agitation at 4° C. for 18 hours with 1 liter of HUVE cell media which had been conditioned for 48 hours. The gel was then poured into a column (5×1.5 cm), washed with four volumes of 0.1 N acetic acid made pH 7.5 with ammonium acetate, and the antibody-bound PDGF immunoreactive proteins eluted with 1 N acetic acid. Peak fractions were determined by biological assays and immunoblotting and the fractions pooled.

Initial studies of the PDGF-related growth factors secreted by HUVE cells were done by removing the serum containing growth media from confluent cultures of cells and replacing it with serum-free media. Aliquots of this media were removed periodically and the proteins immunoblotted using an antibody specific for human platelet PDGF. This antibody does not cross-react with any other known growth factors and is able to detect less than 500 picograms of dimeric PDGF or 10 nanograms of reduced, monomeric A or B chain peptide on immunoblots. HUVE cells were grown to confluence in 6 well plates. The growth media was removed, cells washed with PBS and 1 ml of serum-free media was added to each well. The media was removed after conditioning for the period of time from 6–48 hours, dialyzed against 1 N acetic acid and lyophilized. The samples were then run on 12% PAGE, electroblotted to nitrocellulose and visualized with the anti-human PDGF antibody. Five nanograms of purified platelet PDGF was run as reference.

The results indicated constitutive secretion of several species of molecules which are inmmunologically similar to platelet PDGF but are of higher relative molecular weight (36–39 kD) than the expected 30–32 kD MW of platelet PDGF or A chain or B chain homodimers. Chemotactic and mitogenic assays performed with this serum-free conditioned media indicated the total biological activity present was equivalent to 15 ng/ml of platelet PDGF after a 48 hour conditioning period. Incubation of the media with 30 µg/ml of anti-human PDGF IgG neutralized approximately 20–30% of the mitogenic activity and similar amount of the chemotactic activity.

The presence in HUVE culture media of several species of PDGF immunoreactive molecules was unexpected, particularly molecules of higher molecular weight than those of the A and B chain dimeric molecules anticipated to be produced and secreted by endothelial cells (Collins, et al., *Nature,* 328:621–624, 1987; Sitaras, et al., *J. Cell. Physiol.,* 132:376–380, 1987). In order to obtain greater amounts of the PDGF-like proteins for further analysis, the HUVE cells had to be kept in media containing 20% fetal calf serum, since the cells begin to die after 24 hours in serum-free or low serum media. The PDGF immunoreactive proteins were partially purified from the serum containing media by use of an antibody affinity column made with the anti-human PDGF IgG and an Affi-Gel 10 support (BioRad). Mitogenic assays were performed using NRK cells as target cells (PDGF BB=5 ng/ml, PDGF AA=10 ng/ml). HUVE media was 250 µl of HUVE cell serum-free conditioned media (48 hours) which was dialyzed against 1 N acetic acid, lyophilized, and resuspended in DMEM before addition to test wells. Affinity purified fraction was 5 µl/ml of combined, concentrated major pool from Affi-Gel 10 affinity column. Anti-PDGF IgG or non-immune IgG (30 µg/ml) was added to the samples and incubated 18 hours at 4° C. prior to testing in the mitogenic assay. The mean of triplicate samples was determined and the standard deviation was less than 5%. The experiments were repeated at least three times with similar results.

When aliquots of the partially purified proteins were assayed for chemotactic and mitogenic activity, all biological activity could be neutralized by prior incubation of the proteins with the anti-human PDGF antibody. This indicated that the only biologically active molecules present in the partially purified media proteins were PDGF immunorelated molecules.

Aliquots of the partially purified proteins were immunoblotted using the same anti-PDGF antibody and the data indicated the presence of the higher MW molecules observed in the serum-free conditioned media. The major species secreted migrates on polyacrylamide gels at 36 kD and comprises at least 50% of the total immunoreactive protein purified from conditioned media. The immunoreactive species migrating at 37 and 39 kD constitute most of the remaining immunoreactive protein. A similar pattern was seen with proteins labeled with $^{35}$S-cysteine and affinity purified with the anti-PDGF IgG immunoaffinity column. Less than 15% of the total affinity purified proteins co-migrated with purified platelet PDGF or recombinant PDGF isoforms.

Prior incubation of the antibody with purified PDGF (300 ng PDGF/2 µg IgG) blocked antibody binding to all of the molecules, indicating shared antigenic determinants with dimeric platelet PDGF. Interestingly, when the antibody was blocked with recombinant AA, BB, or AB dimers, antibody binding to the HUVE secreted proteins was inhibited equally by all three dimeric forms, suggesting that the antibody recognizes common epitopes present on all three PDGF dimers and the HUVE secreted molecules. In order to insure that none of the antibody binding molecules detected on Western blots was derived from fetal calf serum or other additives in the culture media, a new, unused antibody affinity column was made and media which was never conditioned by cells was processed exactly as the conditioned media. No PDGF immunoreactive molecules were detected in the fractions from this column by immunoblot and no biological activity was detected. When platelet PDGF or the recombinant dimers are reduced with 200 mM dithiothreitol (DTT), monomeric A chain (17 kD) and B chain (14 kD) peptides are observed on immunoblots. Treating the HUVE molecules in a 100 mM DTT sample buffer resulted in slower migration of the major immunoreactive peptides on polyacrylamide gels. Most of the immunoreactive molecules migrated at 38–39 kD and less intense bands were observed at 25 and 14 kD. It was necessary to run at least 10 times as much reduced protein as nonreduced in order to detect the reduced molecules. This is consistent with the affinity of the antibody for monomeric forms of the PDGF A and B chain peptides. These data indicate that the major species in the PDGF-related affinity purified proteins from conditioned media of HUVE cells was monomeric peptide which migrates on acrylamide gels at an apparent molecular weight of 36 kD nonreduced and 38 kD when reduced.

EXAMPLE 2

Biological Assays

Chemotactic activity was determined in the Boyden chamber chemotaxis assay with NIH 3T3 or bovine aortic smooth muscle (BASM) cells as described (Grotendorst, et al., *Proc. Natl. Acad. Sci. USA,* 78:3669–3672, 1981; Grotendorst, et al., *Methods in Enzymol.,* 147:144–152, 1987). Mitogenic assays were performed using 96 well plates and normal rat kidney (NRK) fibroblasts or NIH 3T3 cells as target cells. The cells were plated in DMEM, 10% FCS; NRK cell cultures were used 10–14 days after confluence and 3T3 cells made quiescent by incubation for 2 days in serum-free DMEM, 0.2 mg/ml BSA before use. Sample proteins and dilutions of known standards were added to the wells and the plates incubated at 37° C. in 10% $CO_2$, 90% air for 18 hours, after which $^3$H-thymidine at a final concentration of 5 uCi/ml was added and incubated for an additional 2 hours. The media was removed, the cells washed and DNA synthesis determined from the $^3$H-thymidine incorporation into trichloroacetic acid precipitable material by scintillation counting.

Gel Electrophoresis and Immunoblotting

Electrophoresis was performed on 12% polyacrylamide gels containing SDS (Laemmli, U.K., *Nature,* 227:680–685, 1970) unless otherwise stated. Immunoblotting was performed by electroblotting the proteins to a nitrocellulose membrane and incubating the membrane in 50 mM Tris-HCl, pH 7.4, 100 mM NaCl (TBS) with 5% non-fat dry milk at 25° C. for 1 hour to block non-specific antibody binding. The blocking solution was removed and the antibody (15 µg/ml) added in TBS containing 0.5% non-fat dry milk and 1 µg/ml sodium azide and incubated overnight at 25° C. The membranes were washed 5 times in TBS, 0.5% milk for 10 minutes each wash and then incubated with alkaline phosphatase conjugated affinity purified rabbit anti-goat IgG (KPL, Gaithersburg, Md.) at a 1:1000 dilution in TBS containing 0.5% milk at 25° C. for 1 hour. The filters were washed with TBS five times, 10 minutes each time, and the blot developed using an alkaline phosphatase substrate solution (0.1 M Tris-HCl, pH 9, 0.25 mg/ml nitro blue tetrazolium, 0.5 mg/ml 5 bromo-4-chloro-3-indolyl phosphate).

Major Chemotactic and Mitogenic Activity Is Produced by 36 kD Peptide and Not PDGF Peptides In order to determine if the chemotactic and mitogenic activities observed in the partially purified media proteins were from molecules containing the PDGF A and B chain peptides or were the products of molecules which do not contain these sequences, biological assays were performed with serial dilutions of the affinity purified media proteins and serial dilutions of recombinant PDGF AA and BB homodimers and the AB heterodimer. Sufficient quantities of the samples were prepared to perform the mitogenic and chemotactic assays and the immunoblots with aliquots of each dilution sample. The mitogenic activity of the HUVE affinity purified factors observed was comparable to the activity elicited by all three recombinant PDGF dimers. The chemotactic activity was comparable to the AB heterodimer, producing less response than the BB homodimer and greater response than the AA homodimer. When the biological activity of the samples was compared with immunoblots of equivalent amounts of the same samples, no A chain nor B chain molecules were detected in the test samples. These data demonstrate the major biological activity present in the anti-PDGF affinity purified fraction cannot be accounted for by PDGF A or B chain containing molecules and imply that the major PDGF-immunoreactive protein species present in these samples (the 36 kD peptide) is biologically active and does not contain amino acid sequences found in the amino and carboxy terminals of the PDGF A or B chain peptides.

EXAMPLE 3

Receptor Competition Assays

Assays were performed using confluent cultures of NIH 3T3 cells in 24 well plates (Costar) grown in DMEM, 10% fetal calf serum, 10 µg/ml Gentamicin. The growth media was removed and the cells washed twice with serum-free DMEM, 0.2 mg/ml BSA and the plates placed on ice for 30 minutes in serum-free DMEM, 0.2 mg/ml BSA. Test samples and controls were made up in serum-free DMEM, 0.2 mg/ml BSA containing 5–10 ng/ml of HUVE affinity purified proteins and a serial dilution of one of the recombinant PDGF isoforms in a concentration range of 300 ng/ml to 16 ng/ml. One milliliter aliquots of the samples were placed into wells of the 24 well plates and incubated on ice on a platform rocker for two hours. After the incubation period, the cells were washed three times for 10 minutes each on ice with PBS. The proteins bound to the surface of the cells were eluted with 5 ul of 1 N acetic acid for 10 minutes. The acetic acid elution samples were lyophilized, resuspended in 5 mM HCL, run on 12% polyacrylamide gels and immunoblotted to nitrocellulose using the anti-PDGF antibody.

In order to substantiate the binding of the endothelial cell molecules to the PDGF cell surface receptors, competitive receptor binding assays were performed. Because immunoblots of the affinity purified HUVE cell secreted proteins indicated the presence of multiple PDGF immunoreactive molecules, $^{125}$I-labeled PDGF competition assays could not be used since this would not indicate which molecules in this mixture were competing for binding of the labeled PDGF for the receptors on the target cells. Since the isoforms of PDGF and the major PDGF immunorelated protein secreted by HUVE cells are of different molecular weights, receptor binding competition was demonstrated on immunoblots. Direct binding of the anti-PDGF immunoreactive peptides to NIH 3T3 cells was demonstrated by incubating monolayers of the 3T3 fibroblasts with the anti-PDGF affinity purified proteins (10 ng/ml) for 2 hours at 4° C. Bound peptides were released by washing of the cell layer with 1 N acetic acid and quantitated by immunoblot analysis using anti-PDGF IgG. This data show that the 36 kD immunoreactive peptide binds to cell surface of NIH 3T3 cells. This binding can be competed by increasing concentrations of recombinant PDGF BB added to the binding media. These data suggest that the CTGF peptide binds to specific cell surface receptors on NIH 3T3 cells and that PDGF BB can compete with this binding.

RNA Isolation and Northern Blotting

Total RNA was isolated from cells in monolayer culture cells. Lyophilized RNA was resuspended in gel loading buffer containing 50% formamide and heated at 95° C. for two minutes before loading (20 μg per lane total RNA) onto 2.2 M formaldehyde, 1% agarose gels and run at 50 volts. Integrity of RNA was determined by ethidium bromide staining and visualization of 18S and 28S rRNA bands. After electrophoresis the RNA was transferred to nitrocellulose by blotting overnight with 10× SSC buffer. The nitrocellulose was air dried and baked at 80° C. for 2 hours in a vacuum oven. Hybridization was performed overnight at 46° C. with the addition of 5×10$^5$ CPM per ml of $^{32}$P-labeled probe. Normally for Northern blots, the entire plasmid was labeled and used as a probe. Labeling was done with a random primer labeling kit from Boehringer Mannheim. After hybridization, membranes were washed twice in 2× SSC, 0.1% SDS for 15 minutes each at room temperature, once for 15 minutes in 0.1× SSC, 0.1% SDS, room temperature and a final 15 minutes wash in 0.1× SSC, 0.1% SDS at 46° C. Blots were autoradiographed at −70° C. on Kodak X-omat film.

EXAMPLE 4

Library Screening, Cloning, and Sequencing

Standard molecular biology techniques were used to subclone and purify the various DNA clones (Sambrook, et al., *Molecular Cloning a Laboratory Manual*, Second edition, Cold Spring Harbor Laboratory Press, Col. Spring Harbor, N.Y.). Clone DB60 was picked from a lambda gt11 HUVE cell cDNA library by induction of the fusion proteins and screening with anti-PDGF antibody. Plaques picked were rescreened and positive clones replated at low titer and isolated.

The EcoR I insert from clone DB60 was cloned into the M13 phage vector and single-stranded DNA obtained for clones with the insert in opposite orientations. These M13 clones were then sequenced by the dideoxy method using the Sequenase kit (U.S. Biochemical) and $^{35}$S-dATP (duPont). Both strands of DNA for this clone were completely sequenced using primer extension and both GTP and ITP chemistry. Aliquots of the sequencing reactions were run on both 6% acrylamide (16 hours) and 8% acrylamide (6 hours) gels, vacuum dried and autoradiographed for at least 18 hours.

The cDNA fragment from clone DB60 was $^{32}$P-CTP labeled and used to rescreen the HUVE cell cDNA lambda gt11 library. Several clones were picked and the largest, the 2100 bp clone designed DB60R32, was subcloned into Bluescript phagemid. Subclones were made of Pst I, Kpn I, and Eco RI/Kpn I restriction fragments also in Bluescript. These subclones were sequenced by double-stranded plasmid DNA sequencing techniques using Sequenase as described above. The 1458 bp Eco RI/Kpn I clone containing the open reading frame was subcloned into M13 mp18 and M13 mp19 and both strands of DNA were completely sequenced using single-stranded DNA sequencing techniques with primer extension and both GTP and ITP chemistry.

Cloning Expression and Sequencing of the cDNA for Connective Tissue Growth Factor In order to further characterize these PDGF related molecules, sufficient quantities of the CTGF protein for amino acid sequencing was needed. However, the low concentrations of CTGF in the conditioned media of HUVE cell cultures and the costly and time consuming techniques involved in obtaining and culturing these cells made protein purification to homogeneity and amino acid sequencing impractical. Therefore, the anti-PDGF antibody was used to screen an HUVE cell cDNA library made in the expression vector lambda gt11. Over 500,000 recombinant clones were screened. Several clones which gave strong signals with the anti-PDGF antibody in the screening process were purified and subcloned into the M13 phage vector and partial sequence data obtained by single-stranded DNA sequencing. A search of the GenBank DNA sequence data base indicated that two of the clones picked contained fragments of the PDGF B chain cDNA open reading frame sequence. One of these clones was similar to a 1.8 kb insert previously isolated by Collins, et al. (*Nature,* 316:748–750, 1985) using a c-sis cDNA probe. A third clone of 500 bp was completely sequenced and no match was found in a homology search of all nucleotide and amino acid sequences in GenBank (CEF 10 sequence was not available at that time). This clone was designated DB60. Anti-PDGF antibody binding to the fusion protein produced by the clone DB60 was completely blocked by the affinity purified proteins. A $^{32}$P-labeled probe was made of DB60 and used on a Northern blot of 20 μg of total RNA isolated from HUVE cells. The blot indicated probe hybridization with an mRNA of 2.4 kilobases, which is a message of sufficient size to produce the proteins in the 38 kD molecular weight range seen on the immunoblots of the affinity purified proteins. The DB60 clone was used to rescreen the HUVE cell cDNA lambda gt11 library and the largest clone isolated contained a 2100 base pair insert designated DB60R32. A probe made with the 2100 bp Eco RI insert of clone DB60R32 also hybridized with a single 2.4 kb message in a Northern blot of total RNA from HUVE cells.

EXAMPLE 5

In Vivo Transcription and Translation

In vitro transcription reactions were done using the 2100 bp cDNA clone DB60R32 in the Bluescript KS vector. The plasmid was cut with Xho I which cuts the plasmid once in the multiple cloning site of the vector 3' to the cDNA insert. The T7 promoter site located 5' to the cDNA insert was used for transcription. The in vitro transcriptions were done with a kit supplied with the Bluescript vector (Stratagene).

In vitro translation reactions were done using nuclease treated rabbit reticulocyte lysate and $^{35}$S-cysteine in a cysteine-free amino acid mix for labeling of the peptide (Promega). The reactions were done in a final volume of 50 ul containing $^{35}$S-cysteine 1 mCi/ml (1200 Ci/mMole, DuPont), and serial dilutions of mRNA from the in vitro transcription reactions in concentrations ranging from 50 to 500 nanograms per reaction tube. The reactions were incubated at 30° C. for 60 minutes. Aliquots of the reactions were run on reduced or nonreduced 12% polyacrylamide electrophoresis gels, dried, and autoradiographed.

Bacterial expression of immunoreactive CTGF peptide was accomplished by subcloning clone DB60R32 into the Eco RI site of the pET 5 expression vector (Studier, et al., Ed. *Academic Press, New York* Vol. 185, 60–89, 1990) in both sense and inverse orientations (as determined by restriction enzyme digest analysis). Cultures of *E. coli* HMS174 cells were grown in M9 media to an OD 600 of 0.7 and the media made 0.4 mM IPTG and incubation continued for 2 hours. The cells were pelleted, lysed, inclusion bodies removed by centrifugation and aliquots of the pellet extracts run on 12% polyacrylamide gels and immunoblotted using the anti-PDGF antibody. The protein produced by clone DB60R32 in the sense orientation produced anti-PDGF immunoreactive peptides in the 36–39 kD MW range while the anti-sense control produced no immunoreactive peptides. The recombinant peptides produced in the *E. coli* system completely blocked the anti-PDGF reaction with the CTGF peptides present in conditioned media.

Expression of CTGF in Xenopus

For expression in Xenopus oocytes, mature *X. laevis* females were obtained from Nasco (Fort Atkinson, Wis.) and maintained at room temperature. Frogs were anesthetized by hypothermia and the ovarian tissue was surgically removed. Ovarian tissue was minced and digested the 0.2% collagenase (Sigma Type II) in OR-2 without calcium (Wallace, et al., *Exp. Zool.*, 184:321–334, 1973) for 2–3 hours. Unblemished stage VI oocytes (Dumont, *J. Morphol.*, 136:153–180, 1972), 1.3 mm diameter, were then carefully selected and microinjected.

Stage VI oocytes (5–10 at a time) were placed on a hollowed plexiglass platform and drained of excess OR-2 solution. Approximately 50 nl of sample containing 10 ng of RNA was injected into the animal pole just above the oocyte equator using a Leitz system microinjector. Following injection, oocytes were returned to OR-2 buffer with 0.1% BSA and incubated for 24 hours at 25° C. Viable oocytes were then pooled and extracted by homogenization in 100 mm NaCl, 10 mm Tris pH 7.5 with ten strokes of a Dounce homogenizer (20 µl/oocyte). The homogenate was then mixed with an equal volume of freon to remove pigment and lipid and centrifuged at 10,000 rpm for 30 seconds to separate the phases. The top aqueous phase was removed and tested for chemotactic activity using NIH 3T3 cells as described above.

Injection of Xenopus oocytes with 10 ng of RNA preparations derived by in in vitro transcription of the DB60 R32 clone resulted in the production of a fibroblast chemotactic activity. Control injected cells did not produce this activity. These results indicate that the open reading frame of the DB60 R32 clone encodes a protein with chemotactic activity for fibroblastic cells as does CTGF.

EXAMPLE 6

Sequence Analysis of CTGF

The 2100 bp insert of clone DB60R32 was sequenced initially by subcloning of Pst I and Kpn I restriction fragments into Bluescript and using double-stranded dideoxy methods. This indicated an open reading frame of 1047 base pairs and oriented the DB60 insert to the larger cDNA. An Eco RI/Kpn I fragment containing the entire open reading frame was inserted into M13 mp18 and M13 mp19 and both strands of the DNA were sequenced with single-stranded dideoxy methods by primer extension using both GTP and the GTP analog ITP. The cDNA nucleotide sequence of the open reading frame encoded a 38,000 MW protein, confirming the cell-free translation results and matching the size of the immunopurified peptides. A new search of the GenBank data base revealed that this cDNA had a 50% nucleotide sequence homology with CEF-10 mRNA, one of the immediate early genes induced in v-src transformed chicken embryo fibroblasts (Simmons, et al., *Proc. Natl. Acad. Sci. USA*, 86:1178–1182, 1989). The translated cDNA for human CTGF and avian CEF-10 have a 45% overall homology and a 52% homology if the putative alternative splicing region is deleted. This region is between amino acids 171 (aspartic acid) and 199 (cysteine) in the CTGF sequence.

EXAMPLE 7

Analysis of CTGF Promoter Region

Cell Cultures

Human skin fibroblasts were grown from explants of skin biopsy specimens. NIH/3T3 cells and Cos 7 cells were obtained from the American Type Culture Collection (ATCC, Rockville, Md.) All cells were cultured in Dulbecco's modified eagle's medium (DMEM) contained 10% fetal calf serum (FCS) at 37° C. in an atmosphere of 10% $CO_2$ and 90% air. Human skin fibroblasts were used prior to the sixth passage.

Growth Factors

TGF-β 1 was a gift from Richard Assoian (U. Of Miami). Recombinant PDGF BB was obtained from Chiron (Emeryville, Calif.). Purified murine EGF was purchased from Sigma (St. Louis, Mo.).

RNA Isolation and Northern Blotting

Total RNA was isolated from cultured cells by acid guanidium thiocyanate-phenol-chloroform extraction as reported previously (Chomczynski, et al., *Birchem*, 162: 156–159, 1987). Total RNA was electrophoresed on an 1.5% agarose/formaldehyde gel and transferred to nitrocellulose. The CTGF probe as 1.1 kb fragment representing the CTGF open reading frame obtained by PCR reaction using specific primers HO1 5'-CGGAATTCGCAGTGCCAACCATGACC-3' (SEQ ID NO:3) and HO2 5'-CCGAATTCTTAATGTCTCTCACTCTC-3' (SEQ ID NO:4). Hybridizations were performed using $1 \times 10^6$ cpm/ml of these probes labeled with [$^{32}$α-P]dCTP by using a Random Primer DNA Labeling Kit (Boehringer Mannheim Biochemicals, Indianapolis, Inc.). Autoradiography was performed at −70° C. for 6 to 72 hours by using X-ray films and intensifying screens.

Isolation of Genomic Clones and Sequence Analysis

Genomic DNA was isolated from human skin fibroblasts as described previously (Sambrook, et al., *Cold Spring Harbor Laboratory Press*, 9: 14–19, 1989.). Using 4 µg of genomic DNA as a template, a fragment of the CTGF gene was amplified by PCR using primers HO2 and HO3 5'-CGGAATTCCTGGAAGACACGTTTGGC-3' (SEQ ID NO:5). PCR products were digested with EcoRI and subcloned into M13. Sequence analysis by the dideoxy chain termination method (Sanger, et al., *Proc. Natl.Acad.Sci. USA*, 74: 5463–5467, 1977.) Using the Sequenase kit *U.S. Biochemical Corp., Cleveland, Ohio) demonstrated 900 bp fragment which had a 387 bp intern in the middle portion. Using a Human Genomic Library in the Lambda FIX™ II vector (Stratagene, La Jolla, Calif.) we screened approximately $1 \times 10^6$ recombinant phages with $^{32}$P-labeled 900 bp genomic DNA fragment as probe and isolated 3 phage clones that contained the CTGF gene.

Luciferase Reporter Gene Assays

A fragment of the CTGF promoter containing nucleotides −823 to +74 from one of the human genomic clones was first cloned in the Sac1-Xho1 cloning site of pGL2-Basic vector (Promega). This construct (PO) was used as a template for PCR and deletion mutants were made with specific primers as follows: P1 contained nucleotides from −638 to +74, P2 from −363 to +74, P3 from −276 to +74, and P4 from −128 to +74. All deletion fragments were sequenced to insure no mutations had been introduced in the promoter fragments. NIH/3T3 cells were transfected in a 6-well plate with LIPOFECTIN® reagent (GIBCO BRL) for 6 hours. Each transfection included 2 µg of pSV-β-Galactosidase vector (Promega). Cells were incubated in serum-free DMEM with ITS™ (Collaborative Biomedical Products) for 24 hours after transfection followed by the incubation with growth factors for 4 hours or 24 hours. Luciferase activity was measured by using Luciferase Assay System (Promega) and a scintillation counter (Beckman LS6000SC) using it in single photon monitor mode. To normalize for differences in transfection efficiency β-galactosidase activity was measured using a chemiluminescent assay using Galacto-Light™ (TROPIX, Inc.).

Preparation of Nuclear Extracts

Nuclear extracts were prepared as described by Abmayr and Workman (Current Protocols in Molecular Biology, vol 2, pp12.1.1–12.1.9, Ausubel, et al., *Greene Publ., and Wiley Interscience, New York, N.Y. Briefly,* cells were treated with hypotonic buffer (10 mM HEPES pH 7.9, 1.5 mM $MgCl_2$, 10 mM KCl, 0.2 mM PMSF, 0.5 mMDTT), homogenized with 10 strokes of a glass dounce homogenizer and nuclei were isolated by centrifugation at 3300×g for 15 minutes. Nuclear proteins were extracted by suspending the nuclei in an equal volume of extraction buffer (20 mM HEPES pH7.9, 25% glycerol, 1.5 mM $MgCl_2$, 0.8M KCl, 0.2 mM EDTA, 0.2 mM PMSF and 0.5 mM DTT). The extract w as dialyzed against 20 mM HEPES pH 7.9, 20% glycerol, 100 mM KCl, 0.2 mM EDTA, 0.2 mM PMSF and 0.5 mM DTT before use. Protein concentration was determined using the BCA protein assay regent (Pierce).

Gel Mobility Shift Assay

Fragments of the CTGF promoter were prepared by PCR or restriction endonuclease digestion of the promoter fragment. Double stranded oligonucleotides were prepared by annealing complementary single stranded oligonucleotides. All oligonucleotides and fragments were checked by electrophoresis in agarose gels or polyacrylamide gels. Radiolabeled fragments of the CTGF promoter were prepared by end-labeling with Klenow enzyme (Boehringer Manheim) and polynucleotide kinase (Boebringer Manheim). Labeled fragments were purified by electrophoresis in 2% agarose gels or 20% polyacrylamide gel before use in gel mobility shift assay. The binding reaction mixture contained 1 µg of nuclear extract protein in 20 µl of 10 mM HEPES pH 7.9, 5 mM Tris, 50 mM KCl, 0.1 mM EDTA, 1 µg poly(dI-dC) poly(dI-dC) (Phamacia), 10% glycerol, 300 µg/ml BSA, and 10,000 cpm $^{32}$P labeled DNA probe. Unlabeled competitor DNA was added and incubated at 4° C. for 2 hours prior to adding the labeled probe. The labeled probe was incubated for one hour at 4° C. in the reaction mixture. Electrophoresis was performed using 5% polyacrylamide gel with 50 mM Tris, 0.38M glycine and 2 mM EDTA.

Methylation Interference Assay

End-labeled fragments of double stranded oligonucleotides were prepared as described for the gel mobility shift assay. The oligonucleotides were methylated by dimethyl sulfate (Fisher Scientific) for 5 minutes at room temperature. DNA-protein binding and gel mobility shift assay were performed as described above using large amounts of labeled probe (100K cpm) and nuclear protein (20 µg). DNA from shifted and non-shifted bands was purified and cleaved with piperidine (Fisher Scientific), and the samples were electrophoresed on a polyacrylamide DNA sequencing gel. The sequences of the shifted and non-shifted fragments were compared with the intact probe sequenced using the same methods.

EXAMPLE 8

Prolonged Induction of CTGF mRNA by Short Term TGF-β Exposure

Most immediate early genes, such as c-fos and c-myc, that are induced by growth factors exhibit a short burst of expression even though the growth factor remains present in the media. In contrast, CTGF transcripts remain at high levels for over 24 hours after activation of the cells with TGF-β (Igarashi, et al., *Mol. Biol Cell,* 4: 637–645, 1993). This example examines whether the long term elevation of CTGF transcripts was dependent on the continuous presence of TGF-β.

Figure 2A:
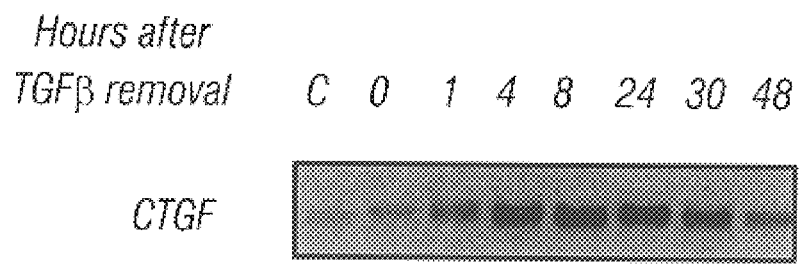
FIGS. 2A–2C shows a Northern blot analysis. Panel (A) shows prolonged induction of CTGF mRNA by short term TGF-β. Confluent cultures of human skin fibroblasts were incubated with DMEM-ITS containing 5 μg/ml of Insulin, 5 μg/ml of Transferrin and 5 ng/ml of Selenium for 24 hours prior to the addition of TGF-β. After the treatment with 10 ng/ml of TGF-β for 1 hour, cells were washed with PBS and incubated with DMEM-ITS for indicated time periods. Panel (B) shows the effect of cycloheximide (CHX) on induction of CTGF mRNA. Lane A and H are non-treated control cells at 4 hours and 24 hours, respectedly. Lane B, 4 hrs. Cycloheximide (10 ug/ml); Lane C, 4 hrs TGF-β present for 1 hour during hour 1 of 2 of cycloheximide exposure; Lane E, same as B with RNA prepared 24 hours after addition of cycloheximide; Lane f, 24 hours TGF-β (10 ug/ml); Lane G, same as D with RNA prepared 24 hours after addition of cycloheximide and 22 hours after removal of TGF-β. Panel (C) shows the effect of protein synthesis inhibitors on induction of CTGF mRNA. Cells were treated with puromycin or anisomycin for 4 hours. TGF-β was added 1 hour after the addition of protein synthesis inhibitor and cells were incubated for 3 hours prior to isolation of total RNA. CTGF transcripts were analyzed by Northern blot as described in the EXAMPLES.

Confluent human skin fibroblasts were cultured in serum free DMEM supplemented by insulin, transferrin, and selenium (DMEM-ITS) for 24 hours prior to adding of TGF-β. After 1 hour exposure to TGF-β, cells were washed in PBS and replaced with DMEM-ITS followed by different periods of incubation. Specifically, confluent cultures of human skin fibroblasts were incubated with DMEM-ITS containing 5 µg/ml of insulin, 5 µg/ml of transferrin and 5 ng/ml of selenium for 24 hours prior to the addition of TGF-β. After the treatment with 10 ng/ml of TGF-β for 1 hour, cells were washed with PBS and incubated with DMEM-ITS for indicated time periods. Northern blot analysis revealed CTGF mRNA was strongly induced from 4 hours to 30 hours after TGF-β removal (FIG. 2A).

Figure 2B:
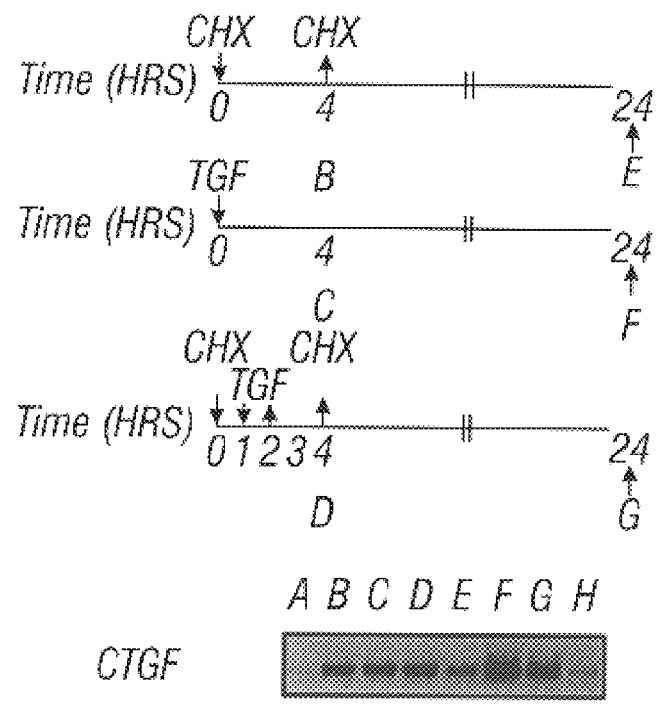

The ability of TGF-β to induce the CTGF transcript in the presence of several protein synthesis inhibitors was examined. FIG. 2B shows the effect of cycloheximide on induction of CTGF mRNA. Lane A and H are non-treated control cells at 4 hours and 24 hours, respectedly. Lane B, 4 hrs. Cycloheximide (CHX) (10 ug/ml); Lane C, 4 hrs TGF-β present for 1 hour during hour 1 of 2 of cycloheximide exposure; Lane E, same as B with RNA prepared 24 hours after addition of cycloheximide; Lane f, 24 hours TGF-β (10 ug/ml); Lane G, same as D with RNA prepared 24 hours after addition of cycloheximide and 22 hours after removal of TGF-β.

As shown in FIG. 2B, a 1 hour stimulation by TGF-β in the presence of cycloheximide was sufficient to induce CTGF mRNA 4 hours later as well as 24 hours later. Cycloheximide alone was able to increase CTGF mRNA 4 hours later, suggesting the possibility of mRNA stabilization as has been reported for cycloheximide induction of other transcripts such as c-fos and c-myc (Greenberg, et al., *Nature* (*London*), 311: 433–438, 1984; Kruijer, et al., *Nature,* 312: 711–716, 1984). However, a report by Edwards and Mahadevan (Edwards, D. R., and L. C. Mahadevan, *EMBO J,* 11:2415–2424, 1992) indicated that the protein synthesis inhibitors cycloheximide and anisomycin, but not puromycin, could act to stimulate transciption of the c-fos and c-jun genes, therefore message stabilization is not the only possible mechanism of action for these compounds.

Figure 2C:
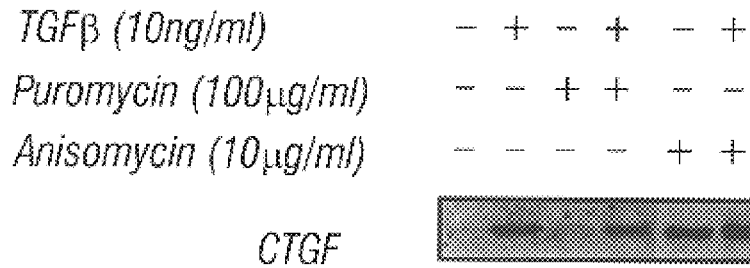

The ability of anisomycin and puromycin to inhibit TGF-β induction of CTGF transcripts was compared with that of cycloheximide as to the ability to elevate CTGF transcripts. FIG. 2C shows the effect of protein synthesis inhibitors on induction of CTGF mRNA. Cells were treated with puromycin or anisomycin for 4 hours. TGF-β was added 1 hour after the addition of protein synthesis inhibitor and cells were incubated for 3 hours prior to isolation of total RNA. CTGF transcripts were analyzed by northern blot.

Puromycin did not induce the CTGF mRNA at any of the concentrations tested up to 100 µg/ml, which is 10 fold higher than that needed to completely block protein synthesis in these cells. Even at this high concentration it had no effect on the ability of TGF-β to induce the CTGF mRNA. In contrast, anisomycin did elevate CTGF transcripts (FIG. 2C) as was seen with cycloheximide although TGF-β treatment still raised the level of CTGF mRNA in the presence of anisomycin.

These findings are similar to those reported by Edwards and Mahadevan (Edwards, D. R., and L. C. Mahadevan., *EMBO J*, 11:2415–2424, 1992) where both c-fos and c-jun were induced by anisomycin or cycloheximide by themselves, but not by puromycin alone. These data strongly suggest TGF-β directly regulates CTGF gene expression via a mechanism that is independent of protein synthesis and may be primarily acting at the level of transcription.

EXAMPLE 9

Isolation of the Human CTGF Gene

To elucidate the structure of the CTGF gene, a fragment of the CTGF gene was first obtained using PCR. Four micrograms of genomic DNA prepared from human skin fibroblasts was used as a template and oligonucleotides, HO2 and HO3, were used as primers. After 30 cycles of reaction, a 900 bp fragment was recovered that was 390 bp longer than predicted from the cDNA sequence. Nucleotide sequence analysis of this fragment (HO900) revealed the presence of a 387 bp intron in the middle portion of the fragment. Using HO900 as a probe, 3 phage clones were from the human genomic library that contained a 4.3 kb Xba1 fragment which represented the entire coding sequence of the CTGF gene and a large portion of the putative promoter region. As shown in FIG. 1A, the CTGF gene has 5 exons and 4 introns. A TATA sequence is present 24 nucleotides upstream of the mRNA cap site, determined by oligonucleotide primer extension. The consensus sequence of a CArG box, which is the inner core of the serum response element (SRE) characterized by CC(A/T)$_6$GG, is present between nucleotide position −380 to −390. Other potential regulatory elements are also present including a CAT box, two Sp1 sites and two AP-1 sites. Furthermore, the CTGF promoter has a NF-1 like site, (TGGN$_6$GCCAA) (SEQ ID NO:6), between positions −194 and −182, and TGF-β inhibitory element like sequence (GNNTTGGTGA) (SEQ ID NO:7) between positions −119 and −128. Both of these elements have single base differences from the reported consensus sequences (Edwards, D. R., and J. K. Heath, *The hormonal control regulation of gene transcription*, 16: pp 333–347) DNA sequence comparison showed that the human CTGF promoter has an 80% sequence identity to the murine fisp-12 promoter in the region 300 nucleotides 5' of the transcription start site (FIG. 1B). Further upstream regions exhibit much less similarity in DNA sequence.

EXAMPLE 10

Studies on the CTGF Promoter

To test whether the 5' nontranslated region of CTGF gene functions as a TGF-β inducible promoter, a fusion gene was constructed containing the CTGF promoter (nucleotides −823 to +74; nucleotides 1 to 897, SEQ ID NO: 1) and the coding region of the firefly luciferase gene in the vector pGL2-basic. Luciferase activity was tested in a transient transfection assay using NIH/3T3 cells. This construct conferred a 15–30 fold induction of luciferase activity after 24-hour stimulation by TGF-β compared with control cultures. As seen at the level of the CTGF mRNA, other growth factors such as PDGF, EGF and FGF stimulated only a 2–3 fold induction of luciferase activity under identical conditions (Table 1).

TABLE 1

CELL TYPE AND GROWTH FACTOR REGULATION
OF THE CTGF PROMOTER
RELATIVE FOLD INDUCTION OF LUCIFERASE ACTIVITY
AFTER GROWTH FACTOR TREATMENT

| CELL TYPE | TGF-β | PDGF | FGF | EGF |
|---|---|---|---|---|
| NIH/3T3 | 25.7 | 2.9 | 3.3 | 1.4 |
| HSF | 9.2 | 2.4 | 3.1 | 2.2 |
| VSMC | 9.8 | ND | ND | ND |
| HBL 100 | 1.1 | ND | 1.3 | 1.4 |
| HEP G2 | 1.3 | ND | 1.4 | 1.8 |

ND Not Determined
HSF-Human foreskin fibroblasts (primary)
VSMC-Fetal bovine aortic smooth muscle cells (primary)
HBL 100 Human breast epithelial cell line (non-tumorigenic)
HEP G2 Human Hepatic epithelial cell line (non-tumorigenic)
(A CTGF gene fragment extending from nucleotides position -823 to +74 was inserted in the pGL2-basic vector. Plasmids were transfected with lipofectin for 6 hours and cells were incubated in DMEM-ITS for 16 hours prior to the addition of growth factors. After a 24 hour incubation cell extracts were prepared and luciferase activity measured. Luciferase activities were normalized by measuring β-galactosidase activity expressed from a cotransfected lacZ expression vector, pSV-β-galactosidase vector and compared between growth factor treated cells and non-treated cells. These experiments were repeated 4 times with similar observations. A representative experiment is shown).

When this promoter fragment was cloned in the reverse orientation (+74 to −823), only basal levels of luciferase activity were detected and this level was uneffected by TGF-β or other growth factor treatment of the cells. The same pattern of growth factor induction was observed when human skin fibroblasts were used instead of NIH/3T3 cells (Table 1). TGF-β did not induce luciferase activity in several epithelial cell lines (Table 1), demonstrating that TGF-β regulation of the CTGF gene is cell type specific. The lack of any response by the epithelial cells is not due to a lack of a TGF-β response as the growth of these cells is inhibited by TGF-β (10 ng/ml). The induction of luciferase activity under the control of the CTGF promoter only required a brief exposure of the cells to TGF-β as a 1 hour treatment of the cells with TGF-β gives nearly the same fold induction at 4 and 24 hours as cells continuously exposed to TGF-β (Table 2). These results confirm the data from the Northern blots described previously and demonstrate that transcriptional regulation plays a primary role in the control of CTGF gene expression by TGF-β.

TABLE 2

SHORT TERM TGF-B EXPOSURE STIMULATES
LONG TERM CTGF PROMOTER ACTIVITY[1]

| Duration of TGF-β exposure | Time of Assay of Luciferase Activity | |
|---|---|---|
| | 4 Hours | 24 Hours |
| Continuous | 3.8 | 21 |
| 1 hour | 3.5 | 19 |

[1]Fold induction of Luciferase activity determined as described in Table 1 legend and EXAMPLE 7. NIH/3T3 cells were used for these experiments.

EXAMPLE 11

Identification of the Promoter Element Required for TGF-β Induction

Figure 3A:
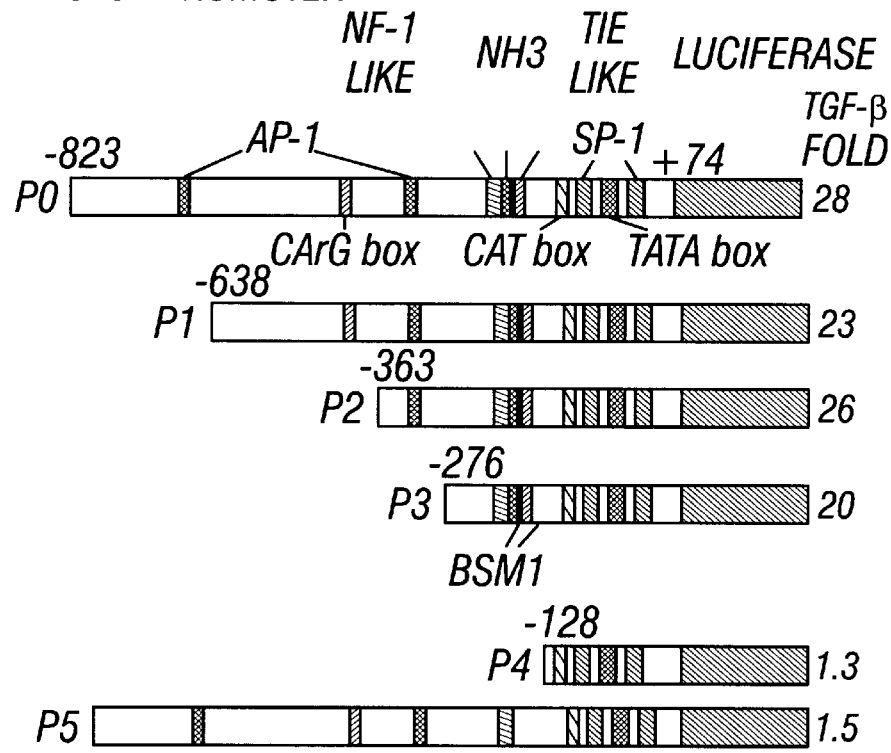
FIG. 3A shows deletion analysis of CTGF promoter-luciferase constructs. Known consensus sequences are indicated. NIH/3T3 fibroblasts were transfected with the constructs and 10 ng/ml of TGF-β was added for activation of the cells and cell extracts were prepared 24 hours later. Relative induction is indicated as fold above non-induced control cells and normalized using the β-galactosidase activity from control plasmids that were cotransfected with the CTGF constructs. These studies were repeated 6 times with similar results. Data represent the average of duplicate transfections with the indicated construct performed in a single set of experiments.

To determine which region of the promoter sequence is responsible for the induction by TGF-β, deletion mutants of the CTGF promoter were constructed using PCR primers designed to delete the known transcription factor consensus elements. Regions of the promoter beginning at the most 5' region and moving toward the transcription start site were systematically deleted (FIG. 3A). Removal of the region of the promoter down to base −363 which included an AP1 site and the CArG box had no significant effect on the TGF-β induction of luciferase activity. Approximately a 30% reduction was seen when the second AP-1 was deleted (−363 to −276) although the fold induction by TGF-βwas still high (20 fold). Removal of the NF-1 like site in the P4 construct (−276 to −128) eliminated the TGF-β inducibility of the promoter suggesting that this region contained the TGF-β response element. Taking advantage of two BsmI sites we deleted the nucleotides from −162 to −1 10 leaving the remaining portions of the promoter intact. This construct exhibited a complete loss of TGF-β inducibility demonstrating that the sequence between positions −162 and −128 is essential for the TGF-β induction of luciferase activity. This region contains the TGF-β inhibtory element (TIC)-like site and is bordered by the NF-1 like site that others have reported plays a role in TGF-β regulation of α2(I) collagen gene expression (Oikarinen, J., A. Hatamochi, and B. De Crombrugghe., *J. Biol. Chem.* 262:11064–11070, 1987.) And type 1 plaminogen activator inhibitor (PAI-1) gene expression (Riccio, et al., *Mol. Cell Biol*, 12:1846–1855, 1992.).

Figure 3B:
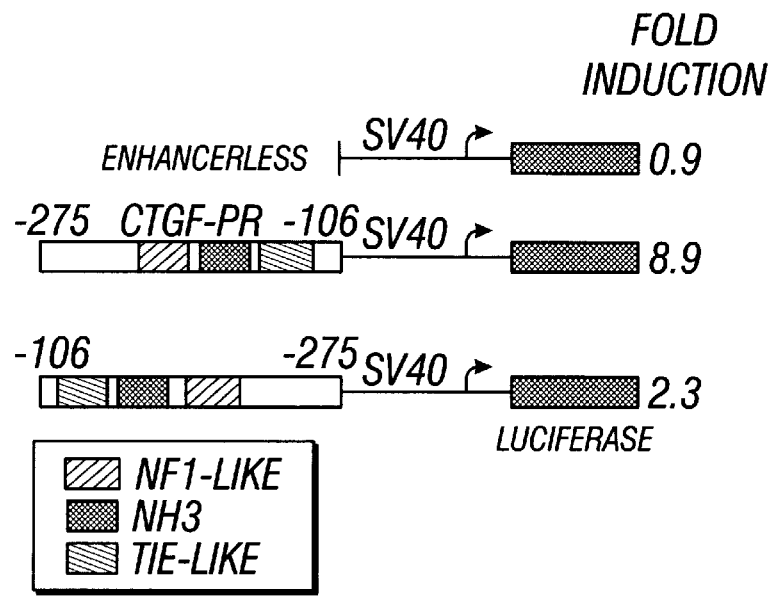
FIG. 3B shows TGF-β response of an SV40 enhancerless promoter element-luciferase reporter construct containing the TGF-β region of the CTGF promoter. The indicated regions of the CTGF promoter were cloned in both orientations upstream from an SV40 enhancerless promoter. Cells were treated with 10 ng/ml of TGF-β for 24 hrs prior to assay for luciferase activity. These experiments were repeated 4 times with similar results. Data represents the average of duplicate transfections of the indicated construct from a single experimental set.

A fusion gene was constructed placing the nucleotides from positions −275 to −106 of the CTGF promoter upstream from an SV40 enhancerless promoter controlling a luciferase gene to determine whether this region of the promoter was sufficient to confer TGF-β inducibility (FIG. 3B). The SV40 enhancerless promoter was not regulated by TGF-β. However, the promoter containing the CTGF sequences −275 to −106 conferred a nearly 9 fold induction after TGF-β treatment. Inversion of the fragment resulted in a little stimulation of luciferase activity after TGF-β treatment. These data confirm that sites in the CTGF promoter between nucleotides −275 and −106 can act as TGF-β regulator elements.

Figure 4:
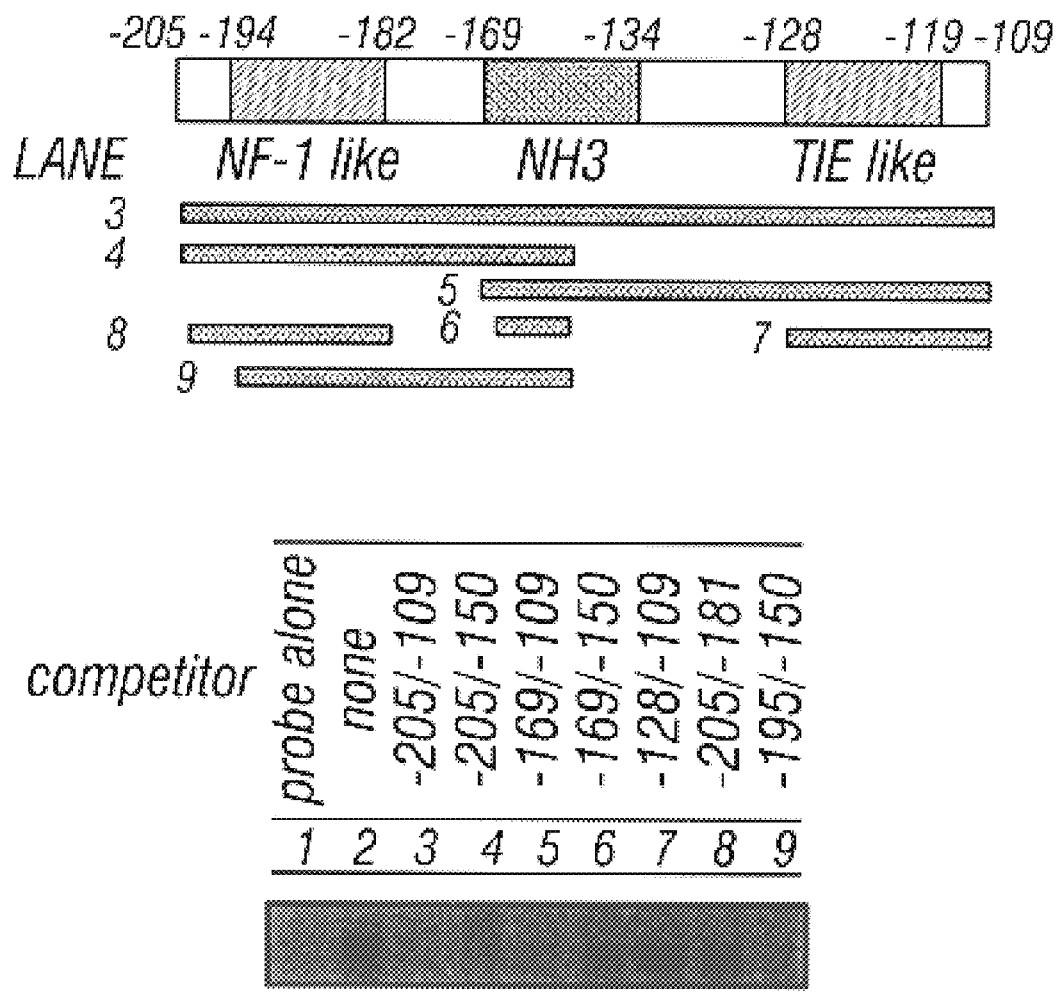
FIG. 4 shows competitive gel shift assays to delineate TGF-β response element in the −205 to −109 region of the CTGF promoter. A nucleotide fragment consisting of the region from −205 to −109 of the CTGF promoter was end labeled with $^{32}$P and used in competitive gel shifts with the indicated oligonucleotides. The specific gel shifted band is indicated by the arrow. A diagram of the sequences used indicates the position of these corresponding to the NF-1 and TIE like elements. The numbered fragments in the diagram indicate the lane number in the competitive gel shift assay with the specific nucleotide sequence indicated above the lane (i.e. 3, −205/−150). Unlabeled competitors were used at a 250 fold molar excess over the labeled fragment. Only oligonucleotides containing the region from −169 to −150 acted as specific competitors. Neither the NF-1 or TIE like regions competed in this assay.

A series of competitive gel shift and methylation interference assays were performed to delineate the region of this potion of the CTGF promoter that was binding to nuclear proteins. Initially competitive gel shifts were used to delineate which region of the sequence between positions −205 to −109 was a target for protein binding. A diagram of the probe and the various competitor fragments is illustrated in (FIG. 4). The results of these studies demonstrate that any fragment that contained the NH3 region (−169 to −149) acted as a specific competitor for the labeled promoter fragment containing bases −204 to −109 (FIG. 4). This region is located between the NF-1 like and TIE like sites. Oligonucleotide fragments that contained only the TIE like region or the NF-1 like region without the NH3 region did not compete in the gel shift assay.

Figures 5A, 5B:
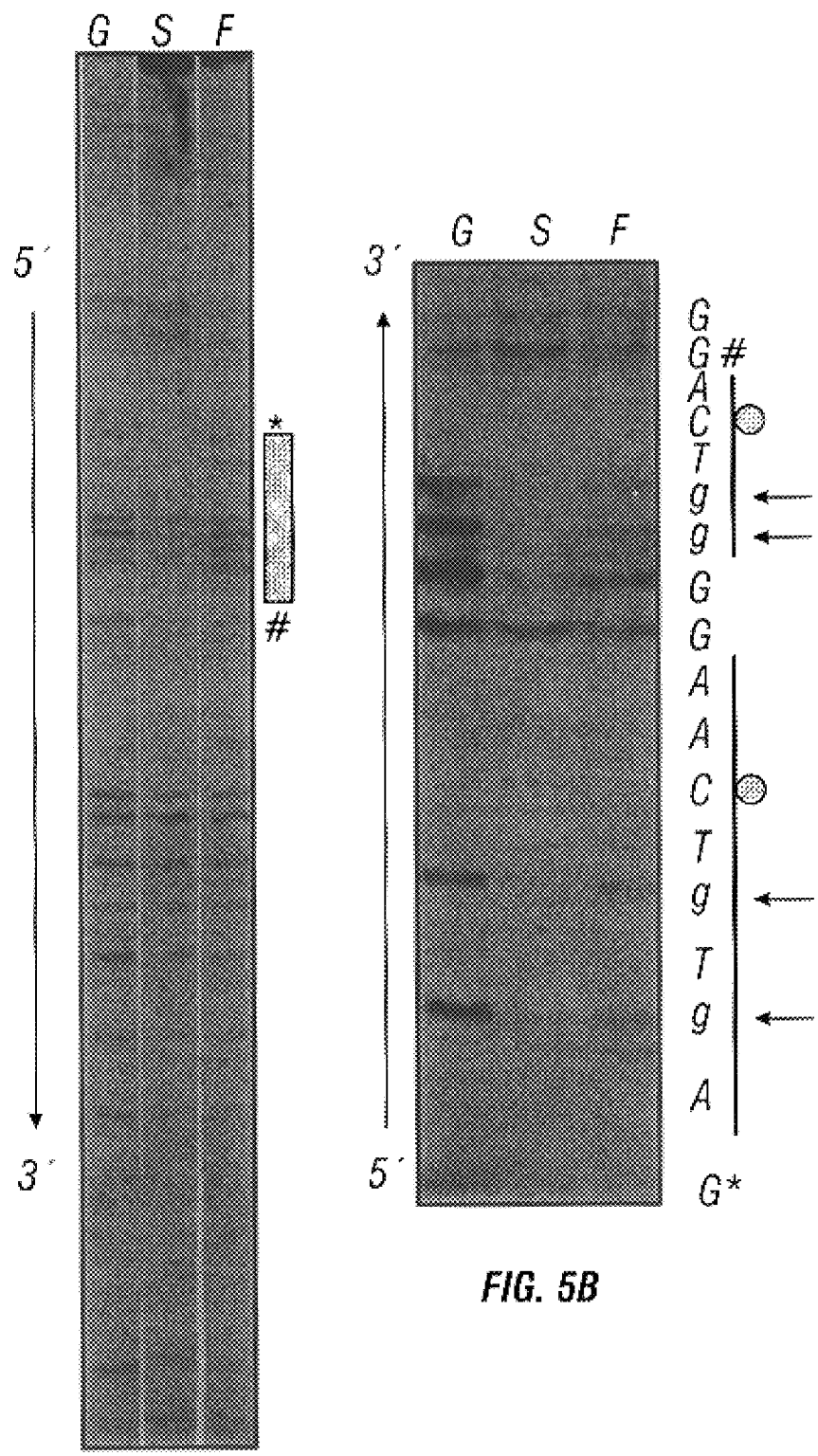
FIG. 5A shows a methylation interference assay of the −205 to −109 region of the CTGF promoter.
FIG. 5B shows a sequence analysis of the region −159 to −142 using a smaller fragment of the promoter (−169 to 193). Lanes are the same as in A. Competed G residues in this sequence are indicated by arrows. Solid circles indicate G residues detected in analysis of complementary strand (data not shown). Symbols * and # are for orientation with sequence in A.

To further delineate the regulatory element, methylation interference assays were performed. A fragment of the promoter from positions −275 to −106 was used initially. The results of these studies indicate that neither the NF-1 like site of the TIE element appear to be interacting with any nuclear proteins present in either control or TGF-β treated cells confirming the gel shift competition data. However, a region between these sites from positions −157 to −145 (nucleotides 669 to 681; SEQ ID NO: 1) contained several G residues that were not methylated in the shifted bands suggesting that this region was the nuclear protein binding site (FIG. 5A). A smaller fragment of the region (nucleotides −169 to −139) was then analyzed to give better resolution of the important G residues (FIG. 5B). The data from this analysis confirmed that of the larger fragment and map G residues that lie within the sequence determined by competition gel shifts.

Figure 6:
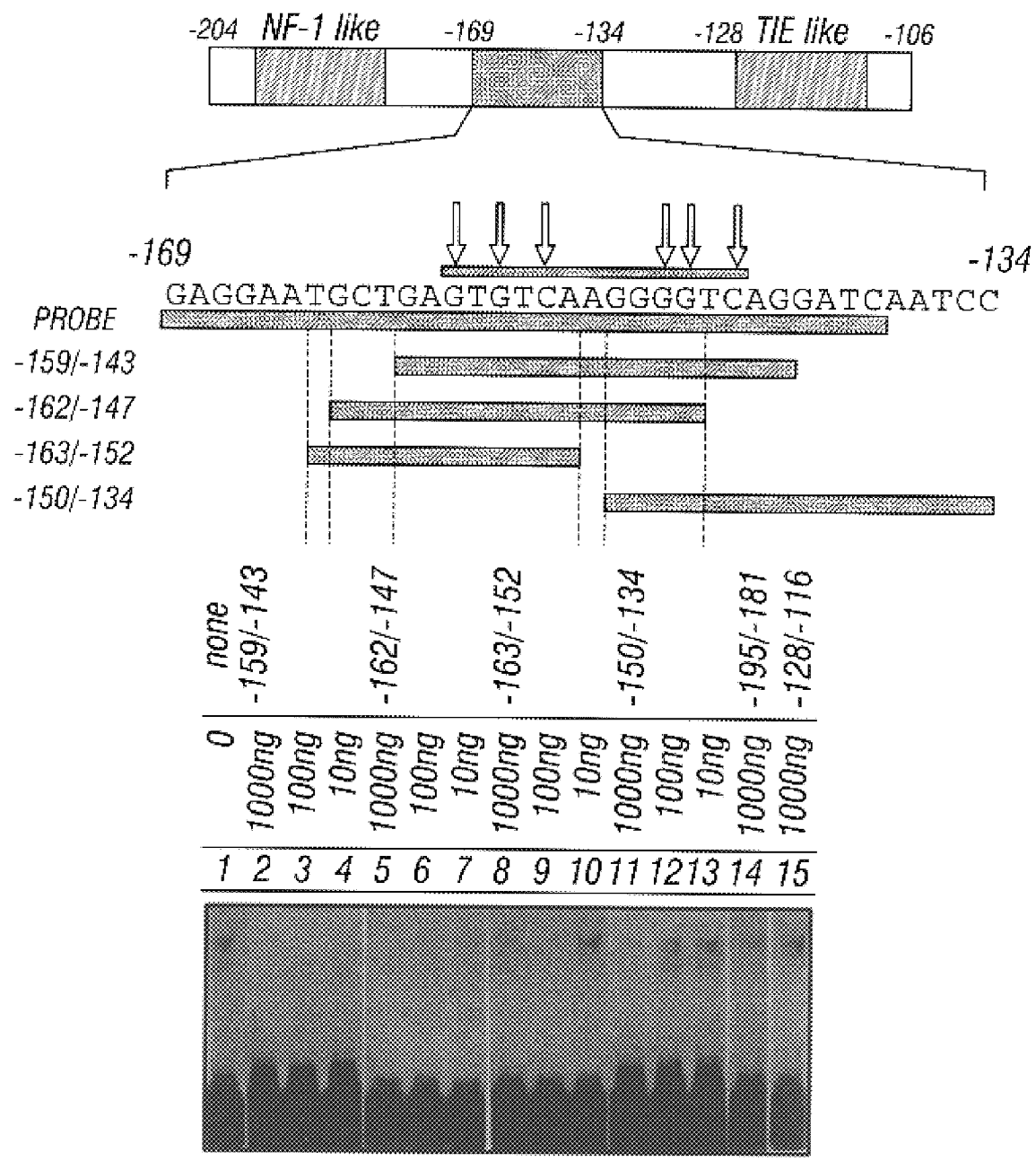
FIG. 6 shows competitive gel shift titration assay of oligonucleotides in the TβRE. Overlapping and non-overlapping oligonucleotides containing portions of the −159 to −143 region of the CTGF promoter were tested in the competitive gel shift assay using a $^{32}$P-end labeled human CTGF promoter fragment (−205 to −109). The intact fragment (−159 to −143) exhibits the highest affinity with complete competition at 10 ng. All other fragments which contain only a portion of this sequence are less effective with the −150 to −134 region being the least effective. Lanes 14 and 15 are the NF-1 and TIE like elements respectively and show no competition at 5000 fold molar excess of labeled probe.

To better characterize the actual TGF-β reactive site, the ability of the intact sequence and several deletions to compete for protein binding was compared in the gel shift assay (FIG. 6). These data confirm the results of the methlyation interference assays and suggest that the region of the promoter from positions −159 to −143 contains at least a portion of the cis regulator element involved in TGF-β regulation of CTGF gene expression.

Point mutations were made in the region of the sequence believed to be involved in the TGF-β induction and tested these promoters in our luciferase reporter construct (FIG. 7). Two point mutations were tested and both reduced the inducibility of the gene by TGF-β. One mutation reduced the induction by 25% from control and the other by 80%. Neither had any effect on basal level of expression compared to control native sequence.

Point mutations were constructed by synthesis of oligonucleotides containing the desired base change and taking advantage of the two BsmI sites in the CTGF promoter. All constructs were confirmed by nucleotide sequence analysis to demonstrate that only the desired base change occurred and that all of the other nucleotide sequence was identical to the normal promoter. Assays were performed as described above for other CTGF promoter-luciferase constructs using NIH/3T3 cells as targets. The data presented in the Table in FIG. 7 is from a single experiment with duplicate assays for each experimental condition. The experiment was run several times to confirm the results. These data demonstrate that a single mutation in this region of the promoter can reduce the TGF-β induction by 85%, to less than 15% of the normal gene. These data demonstrate that the sequence identified is essential for the TGF-β induction of the CTGF gene.

EXAMPLE 12

TGF-β Stimulates Anchorage Independent Growth Via a CTGF Dependent Pathway a. Inhibition of TGF-β Induced CTGF Gene Expression by Elevation of cAMP Levels Both herbimycin and phorbol esters were utilized to determine if either tyrosine kinases or protein kinase C had any role in the regulation of CTGF gene expression induced by TGF-β. These studies were performed using the CTGF promoter (−823 to +74) luciferase reporter construct transfected into NIH/3T3 cells.

NIH/3T3 cells were grown to 50% confluence in DMEM/ 10% FCS. They were all transfected with PO CTGF promoter (nucleotides position −823 to +74) driving the expression of the pGL2 basic vector firefly luciferase using LIPOFECTIN® as described above in EXAMPLE 7. After 24 hours in DMEM/ITS media the inhibitors were added. All of the agents were added to the cultures 2 hours prior to the addition of 10 ng/ml TGF-β. The cells were incubated 24 hours and the luciferase activity determined using the Tropix luciferase assay kit and a Beckman scintillation counter equipped with a single photon monitor. In a related experiment PMA was added to the cells for 24 hours prior to TGF-β to deplete protein kinase C. This also had no effect on the ability of TGF-β to induce luciferase activity under the control of the CTGF promoter. Also, as a control experiment for the herbimycin studies, the activity of this agent to inhibit PDGF induced cell division was examined. Confluent density arrested monolayers of NIH/3T3 cells were treated with the indicated concentrations of herbimycin for 2 hours prior to addition of recombinant PDGF BB. The number of cells was determined by trypsinization and counting 24 hours after the addition of PDGF. The mitotic index represents the percent of cells that underwent mitosis.

Figure 8A:
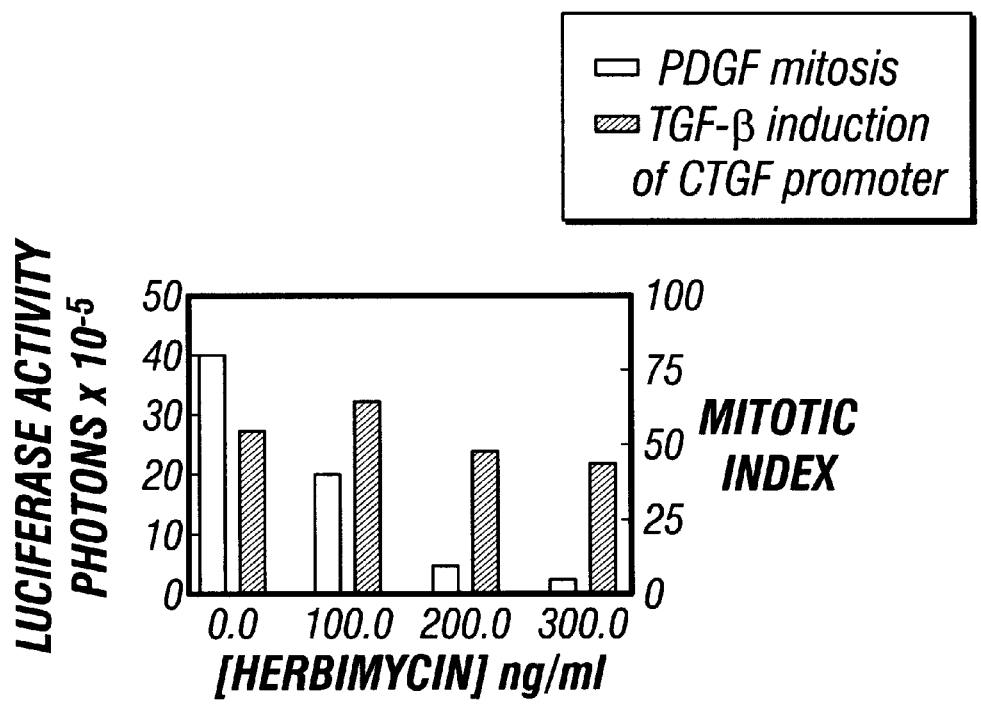
FIGS. 8A –8D show the effect of herbimycin, phorbol ester, cAMP and cholera toxin on TGF-β induced CTGF expression as measured in a luciferase assay.

Neither of these compounds had any effect on the ability of TGF-β to induce CTGF gene expression, nor did they modulate the basal level of CTGF gene expression in the target cells. However, both cholera toxin or 8Br-cAMP were potent inhibitors of the TGF-β induction of the CTGF gene (FIG. 8A).

These data indicate that neither tyrosine kinases or protein kinase C is part of the signal transduction pathway leading to CTGF gene induction controlled by TGF-β. Also, cyclic nucleotide regulated proteins do not appear to be a part of the TGF-β pathway for regulation of CTGF gene expression. However, elevation of cAMP levels in the cell abolishes the TGF-β induction of CTGF gene expression. In a related experiment we find that the cAMP or cholera toxin can be added up 8 hours after addition of TGF-β and it is still effective in blocking the expression of the CTGF gene. This suggests that the action of the cAMP is distal from the receptor and may be effecting transcription factor binding to the CTGF promoter.

b. cAMP Does Not Block All of the Actions of the TGF-β on Fibroblast Cells

Figure 8B:
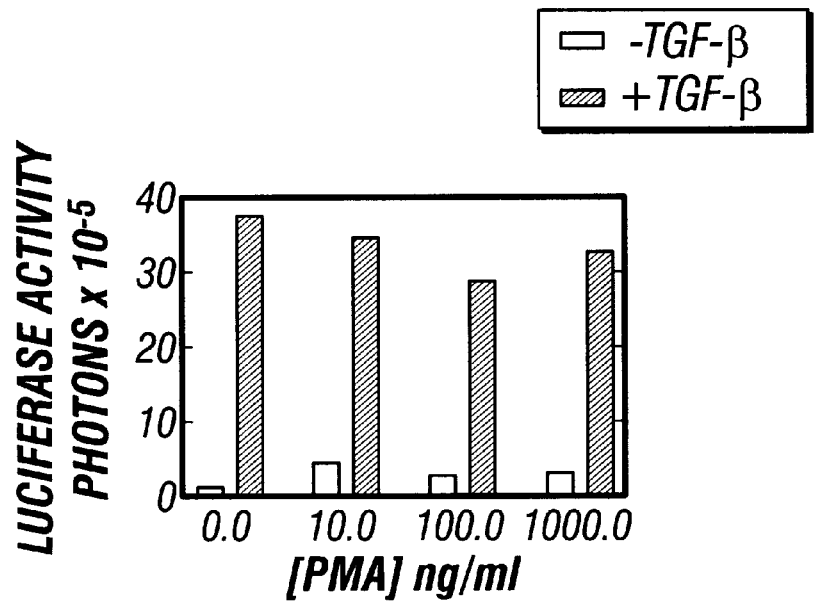
Figure 8C:
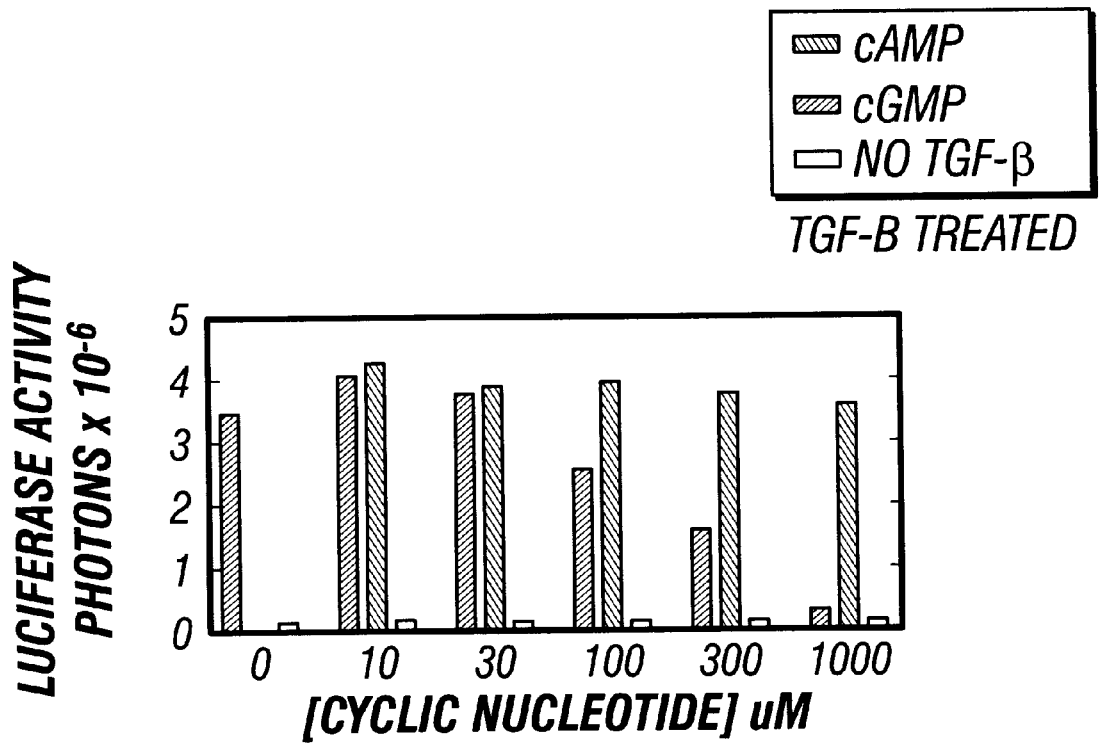
Figure 8D:
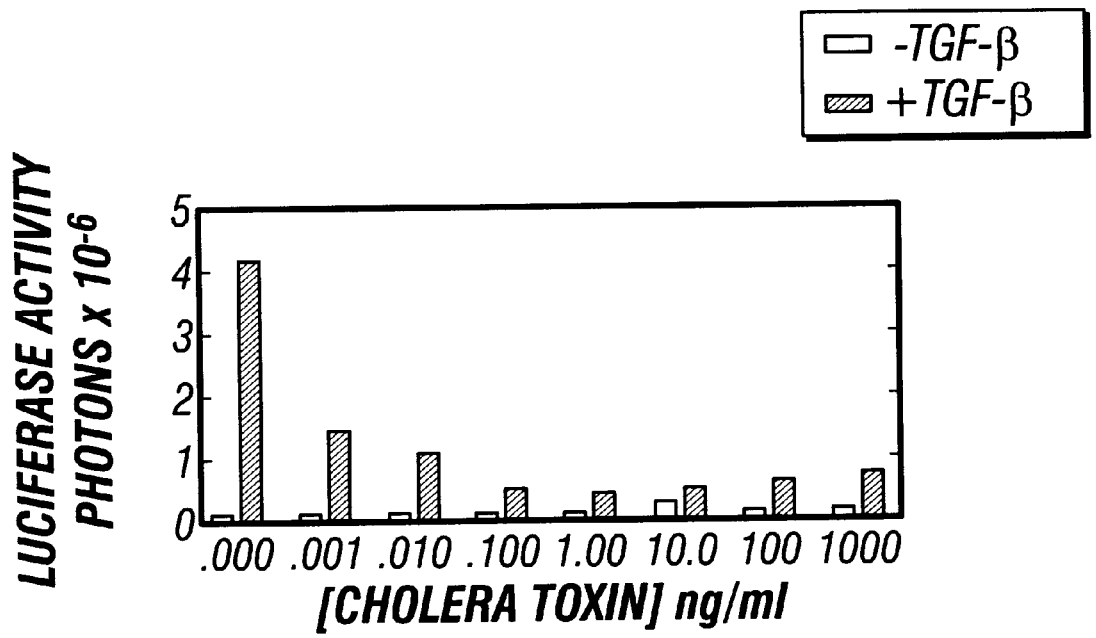
Figure 8E:
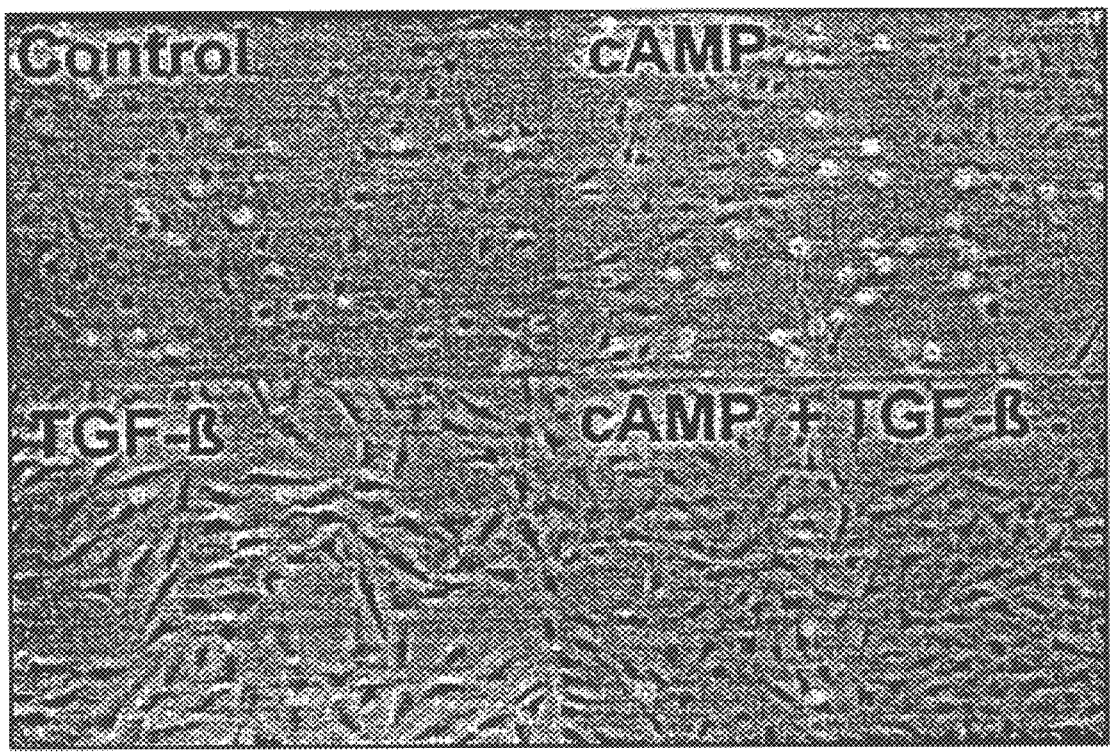
FIG. 8E shows photomicrographs of NIH/3T3 cells either untreated, treated with TGF-β, cAMP (8Br cAMP) or cAMP and TGF-β.
Figure 8F:
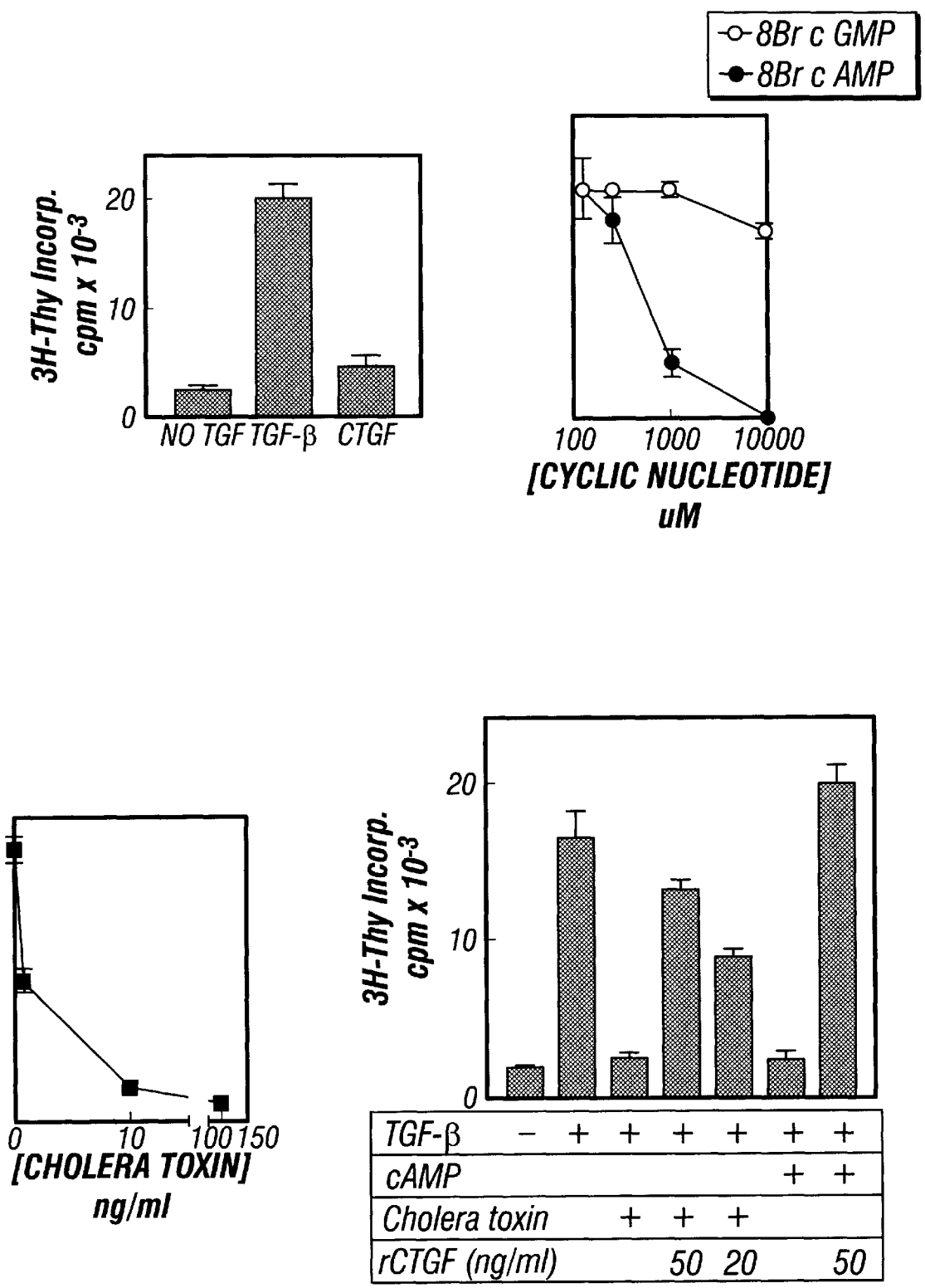
FIG. 8F shows the results of inhibition of anchorage independent growth by 8Br cAMP and cholera toxin, and reversal of cAMP or cholera toxin inhibition of TGF-β induced anchorage independent growth by CTGF.

The four panels shown in FIG. 8B are photomicrographs of the NIH/3T3 cells used in the above experiments which were Control) No Additons; TGF-β) TGF-β (10 ng/ml); cAMP) 8Br cAMP (1000 uM); cAMP+TGF-β) 8Br cAMP (1000 uM) and TGF-β (10 ng/ml) prior to determination of luciferase activity. These data indicate that while cAMP causes dramatic changes in the morphological appearance of the NIH/3T3 cells, TGF-β addition to these cells induces a morphological appearance in these cells which was similar, if not identical, to control cells treated with TGF-β. Thus, although cAMP can block TGF-β induction of CTGF gene expression it has no effect on the biochemical events which regulate the observed changes in morphology seen in these monolayer cultures. These results demonstrate that there are multiple components in the action of TGF-β on fibroblastic cells which can be differentially blocked by cAMP. No significant difference was detected in the culture with respect to total cellular protein content or expression of an SV40/β-galactosidase control reporter gene indicating that the changes were not due to toxic effects of the AMP. Cholera toxin treatment induced a morphology similar to that seen in the 8Br cAMP treated cells which was reversed by addition of TGF-β.

c. Inhibition of TGF-βInduced Anchorage Independent Growth by cAMP and Its Reversal by rCTGF Because of the results of the previous studies, experiments were performed to determine whether cAMP would block TGF-β induced anchorage independent growth. Initially the effects of 8Br cAMP, 8Br cGMP and cholera toxin on the ability of TGF-β to induce anchorage independent growth of NRK cells was examined. Anchorage independent growth assays were performed essentially as described by Guadagna and Assoian (*J Cell Biol*, 115: 1419–1425, 1991). Briefly NRK cells normally maintained as monolayer cultures were plated on an agarose layer in DMEM/10% FCS containing 5 ng/ml EGF. TGF-β or CTGF was added and the cells incubated for 72 hours. DNA synthesis is then determined by labeling for 24 hours with $^3$H-thymindine (2 uCi/ml) the cells harvested and processed by TCA precipitation etc. Inhibitors were added at the same time as the growth factors and remained present for the duration of the experiment (FIG. 8C). (Abbreviations: Cholera toxin (CTX)).

As seen in FIG. 8C both 8Br cAMP and cholera toxin were effective inhibitors of growth in this assay while 8Br cGMP had no effect at concentrations up to 10 mM. Because expression of the CTGF gene was blocked by elevation of cAMP levels in the cells, an experiment was performed to determine whether rCTGF could overcome the inhibition. As seen in the left panel in FIG. 8B addition of rCTGF to NRK cells does not stimulate anchorage independent growth and therefore does not substitute for TGF-β. However, addition of the same amounts of rCTGF to cells treated with TGF-β and inhibited with either 8Br cAMP or cholera toxin overcomes the inhibition and allows the cells to grow at a rate comparable to those treated with TGF-β in the absence of cAMP or cholera toxin (far right panel). These studies suggest a direct link between the production of CTGF and the ability of NRK cells to grow in suspension. They also demonstrate that while TGF-β can induce certain effects in fibroblasts in the presence of elevated levels of cAMP they are not sufficient to allow for anchorage independent growth. Also, since CTGF alone is not sufficient to stimulate this biological response it is not a substitute for all of TGF-β's actions on fibroblasts. These results demonstrate there are both CTGF dependent and CTGF independent effects induced by TGF-β in target cells (NRK) that act synergistically to allow for a specific cellular response (anchorage independent growth).

EXAMPLE 13

Inhibition of TGF-β Induced Granulation Tissue Formation by Agents that Elevate cAMP Levels TGF-β has been shown to induce fibrosis in several animal model studies. For example, one group injected 400 to 800 ng of TGF-β into the subdermnal space in the back of neonatal mice. When the TGF-β is injected once a day for three days in a row, a large area of fibrotic tissue forms (Roberts, et al., *Proc. Natl. Acad. Sci. USA*, 83:4167, 1986). The present example shows comparative studies with TGF-β and CTGF and the results showed that CTGF induced the formation of connective tissue which is very similar, if not identical to that formed in response to TGF-β . Other growth factors such as PDGF or EGF do not induce tissue similar to TGF-β, indicating that CTGF may be responsible for the formation of the tissue induced by TGF-β injection.

Because the results in Example 12 showed that cAMP levels could block the induction of CTGF in the cultured cells, it was of interest to determine whether elevation of cAMP levels in cells in an animal could block the action of TGF-β in vivo. Using the injection model described above and in Roberts, et al., *the following experiment was performed. Neonatal mice were injected once a day for three days in a row with either: TGF-β (400 ng); cholera toxin (100 ng); TGF-β (400 ng) and cholera toxin (100 ng); or saline. Three mice were used in each group. After injected tissue was prepared using standard histological methods, the area of injection was examined by light microscopy after staining with hematoxylin and eosin.

As expected, saline injections had no effect on the type of tissue present in the murine skin and TGF-β injections induced a large amount of new connective tissue which resembled granulation tissue. This tissue contained increased numbers of fibroblasts and increased amounts of collagen and other matrix components. Injection of cholera toxin alone caused no stimulation of granulation tissue formation. Co-injection of TGF-β and cholera toxin also showed no formation of granulation tissue demonstrating that the cholera toxin blocked the TGF-β induced formation of granulation tissue. These results indicate the therapeutic utility of agents that block the production or action of CTGF for use as anti-fibrotic drugs.

SEQUENCE LISTING

<160> NUMBER OF SEQ ID NOS: 9

<210> SEQ ID NO 1
<211> LENGTH: 2970
<212> TYPE: DNA
<213> ORGANISM: Homo Sapiens
<220> FEATURE:
<221> NAME/KEY: CDS
<222> LOCATION: (1025)...(2074)

<400> SEQUENCE: 1

```
tctagagctc gcgcgagctc taatacgact cactataggg cgtcgactcg atcccttttt      60
ctggaaacat tgatggccac tcgtcccttg tccttgccta tataaaactc ctacatatat     120
taagagaaaa ctaagcaaga gttttggaaa tctgccccag gagactgcat cctgagtcac     180
acgagtcttt gttctctttc ttgtcccaaa accgttacct caagtgacaa atgatcaaat     240
ctcaaatata gaattcaggg ttttacaggt aggcatcttg aggatttcaa atggttaaaa     300
gcaactcact cctttctac tctttggaga gtttcaagag cctatagcct ctaaaacgca      360
aatcattgct aagggttggg gggagaaac cttttcgaat tttttaggaa ttcctgctgt      420
ttgcctcttc agctacctac ttcctaaaaa ggatgtatgt cagtggacag aacagggcaa     480
acttattcga aaagaaata agaaataatt gccagtgtgt ttataaatga tatgaatcag      540
gagtggtgcg aagaggatag gaaaaaaaaa ttctatttgg tgctgaaat actgcgcttt      600 ttttttcctt tttttttttt tctgtgagct ggagtgtgcc agctttttca gacggaggaa     660
tgctgagtgt caagggtca ggatcaatcc ggtgtgagtt gatgaggcag gaaggtgggg      720
aggaatgcga ggaatgtccc tgtttgtgta ggactccatt cagctcattg gcgagccgcg     780
gccgcccgga gcgtataaaa gcctcgggcc gcccgcccca aactcacaca caactcttc      840 cccgctgaga ggagacagcc agtgcgactc cacctccag ctcgacggca gccgccccgg      900
ccgacagccc cgagacgaca gcccggcgcg tcccggtccc cacctccgac caccgccagc     960
gctccaggcc ccgcgctccc cgctcgccgc caccgcgccc tccgctccgc ccgcagtgcc    1020
```

```
aacc atg acc gcc gcc agt atg ggc ccc gtc cgc gtc gcc ttc gtg gtc      1069
     Met Thr Ala Ala Ser Met Gly Pro Val Arg Val Ala Phe Val Val
       1               5                  10                  15 ctc ctc gcc ctc tgc agc cgg ccg gcc gtc ggc cag aac tgc agc ggg        1117
Leu Leu Ala Leu Cys Ser Arg Pro Ala Val Gly Gln Asn Cys Ser Gly
            20                  25                  30 ccg tgc cgg tgc ccg gac gag ccg gcg ccg cgc tgc ccg gcg ggc gtg        1165
Pro Cys Arg Cys Pro Asp Glu Pro Ala Pro Arg Cys Pro Ala Gly Val
        35                  40                  45 agc ctc gtg ctg gac ggc tgc ggc tgc tgc cgc gtc tgc gcc aag cag        1213
Ser Leu Val Leu Asp Gly Cys Gly Cys Cys Arg Val Cys Ala Lys Gln
    50                  55                  60 ctg ggc gag ctg tgc acc gag cgc gac ccc tgc gac ccg cac aag ggc        1261
Leu Gly Glu Leu Cys Thr Glu Arg Asp Pro Cys Asp Pro His Lys Gly
65                  70                  75 ctc ttc tgt gac ttc ggc tcc ccg gcc aac cgc aag atc ggc gtg tgc        1309
Leu Phe Cys Asp Phe Gly Ser Pro Ala Asn Arg Lys Ile Gly Val Cys
80                  85                  90                  95 acc gcc aaa gat ggt gct ccc tgc atc ttc ggt ggt acg gtg tac cgc        1357
Thr Ala Lys Asp Gly Ala Pro Cys Ile Phe Gly Gly Thr Val Tyr Arg
                100                 105                 110
```

```
agc gga gag tcc ttc cag agc agc tgc aag tac cag tgc acg tgc ctg       1405
Ser Gly Glu Ser Phe Gln Ser Ser Cys Lys Tyr Gln Cys Thr Cys Leu
            115                 120                 125 gac ggg gcg gtg ggc tgc atg ccc ctg tgc agc atg gac gtt cgt ctg       1453
Asp Gly Ala Val Gly Cys Met Pro Leu Cys Ser Met Asp Val Arg Leu
            130                 135                 140 ccc agc cct gac tgc ccc ttc ccg agg agg gtc aag ctg ccc ggg aaa       1501
Pro Ser Pro Asp Cys Pro Phe Pro Arg Arg Val Lys Leu Pro Gly Lys
    145                 150                 155 tgc tgc gag gag tgg gtg tgt gac gag ccc aag gac caa acc gtg gtt       1549
Cys Cys Glu Glu Trp Val Cys Asp Glu Pro Lys Asp Gln Thr Val Val
160                 165                 170                 175 ggg cct gcc ctc gcg gct tac cga ctg gaa gac acg ttt ggc cca gac       1597
Gly Pro Ala Leu Ala Ala Tyr Arg Leu Glu Asp Thr Phe Gly Pro Asp
                180                 185                 190 cca act atg att aga gcc aac tgc ctg gtc cag acc aca gag tgg agc       1645
Pro Thr Met Ile Arg Ala Asn Cys Leu Val Gln Thr Thr Glu Trp Ser
            195                 200                 205 gcc tgt tcc aag acc tgt ggg atg ggc atc tcc acc cgg gtt acc aat       1693
Ala Cys Ser Lys Thr Cys Gly Met Gly Ile Ser Thr Arg Val Thr Asn
            210                 215                 220 gac aac gcc tcc tgc agg cta gag aag cag agc cgc ctg tgc atg gtc       1741
Asp Asn Ala Ser Cys Arg Leu Glu Lys Gln Ser Arg Leu Cys Met Val
225                 230                 235 agg cct tgc gaa gct gac ctg gaa gag aac att aag aag ggc aaa aag       1789
Arg Pro Cys Glu Ala Asp Leu Glu Glu Asn Ile Lys Lys Gly Lys Lys
240                 245                 250                 255 tgc atc cgt act ccc aaa atc tcc aag cct atc aag ttt gag ctt tct       1837
Cys Ile Arg Thr Pro Lys Ile Ser Lys Pro Ile Lys Phe Glu Leu Ser
                260                 265                 270 ggc tgc acc agc atg aag aca tac cga gct aaa ttc tgt gga gta tgt       1885
Gly Cys Thr Ser Met Lys Thr Tyr Arg Ala Lys Phe Cys Gly Val Cys
            275                 280                 285 acc gac ggc cga tgc tgc acc ccc cac aga acc acc acc ctg ccg gtg       1933
Thr Asp Gly Arg Cys Cys Thr Pro His Arg Thr Thr Thr Leu Pro Val
            290                 295                 300 gag ttc aag tgc cct gac ggc gag gtc atg aag aag aac atg atg ttc       1981
Glu Phe Lys Cys Pro Asp Gly Glu Val Met Lys Lys Asn Met Met Phe
305                 310                 315 atc aag acc tgt gcc tgc cat tac aac tgt ccc gga gac aat gac atc       2029
Ile Lys Thr Cys Ala Cys His Tyr Asn Cys Pro Gly Asp Asn Asp Ile
320                 325                 330                 335 ttt gaa tcg ctg tac tac agg aag atg tac gga gac atg gca tga           2074
Phe Glu Ser Leu Tyr Tyr Arg Lys Met Tyr Gly Asp Met Ala
                340                 345 agccagagag tgagagacat taactcatta gactggaact tgaactgatt cacatctcat     2134
ttttccgtaa aaatgatttc agtagcacaa gttatttaaa tctgtttttc taactggggg     2194
aaaagattcc cacccaattc aaaacattgt gccatgtcaa acaaatagtc tatcttcccc     2254
agacactggt ttgaagaatg ttaagacttg acagtggaac tacattagta cacagcacca    2314
gaatgtatat taaggtgtgg ctttaggagc agtgggaggg taccggcccg gttagtatca     2374
tcagatcgac tcttatacga gtaatatgcc tgctatttga agtgtaattg agaaggaaaa     2434
ttttagcgtg ctcactgacc tgcctgtagc cccagtgaca gctaggatgt gcattctcca     2494
gccatcaaga gactgagtca agttgttcct taagtcagaa cagcagactc agctctgaca     2554
ttctgattcg aatgacactg ttcaggaatc ggaatcctgt cgattagact ggacagcttg     2614
tggcaagtga atttgcctgt aacaagccag attttttaaa atttatattg taaatattgt    2674
```

-continued

```
gtgtgtgtgt gtgtgtgtat atatatatat atatgtacag ttatctaagt taatttaaag    2734
ttgtttgtgc ctttttattt ttgtttttaa tgctttgata tttcaatgtt agcctcaatt    2794
tctgaacacc ataggtagaa tgtaaagctt gtctgatcgt tcaaagcatg aaatggatac    2854
ttatatggaa attctgctca gatagaatga cagtccgtca aaacagattg tttgcaaagg    2914
ggaggcatca gtgtcttggc aggctgattt ctaggtagga aatgtggtag ctcacg        2970
```

<210> SEQ ID NO 2
<211> LENGTH: 349
<212> TYPE: PRT
<213> ORGANISM: Homo Sapiens

<400> SEQUENCE: 2

```
Met Thr Ala Ala Ser Met Gly Pro Val Arg Val Ala Phe Val Val Leu
 1               5                  10                  15

Leu Ala Leu Cys Ser Arg Pro Ala Val Gly Gln Asn Cys Ser Gly Pro
                20                  25                  30

Cys Arg Cys Pro Asp Glu Pro Ala Pro Arg Cys Pro Ala Gly Val Ser
            35                  40                  45

Leu Val Leu Asp Gly Cys Gly Cys Cys Arg Val Cys Ala Lys Gln Leu
        50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320
```

```
Lys Thr Cys Ala Cys His Tyr Asn Cys Pro Gly Asp Asn Asp Ile Phe
            325                 330                 335

Glu Ser Leu Tyr Tyr Arg Lys Met Tyr Gly Asp Met Ala
            340                 345

<210> SEQ ID NO 3
<211> LENGTH: 26
<212> TYPE: DNA
<213> ORGANISM: Artificial Sequence
<220> FEATURE:
<223> OTHER INFORMATION: PCR primer H01

<400> SEQUENCE: 3
cggaattcgc agtgccaacc atgacc                                          26

<210> SEQ ID NO 4
<211> LENGTH: 26
<212> TYPE: DNA
<213> ORGANISM: Artificial Sequence
<220> FEATURE:
<223> OTHER INFORMATION: PCR primer H02

<400> SEQUENCE: 4
ccgaattctt aatgtctctc actctc                                          26

<210> SEQ ID NO 5
<211> LENGTH: 26
<212> TYPE: DNA
<213> ORGANISM: Artificial Sequence
<220> FEATURE:
<223> OTHER INFORMATION: PCR primer H03

<400> SEQUENCE: 5
cggaattcct ggaagacacg tttggc                                          26

<210> SEQ ID NO 6
<211> LENGTH: 14
<212> TYPE: DNA
<213> ORGANISM: Artificial Sequence
<220> FEATURE:
<223> OTHER INFORMATION: NF-1 like site
<220> FEATURE:
<221> NAME/KEY: misc_difference
<222> LOCATION: (4)...(9)
<223> OTHER INFORMATION: Each N can be A, G, T or C.

<400> SEQUENCE: 6
tggnnnnnng ccaa                                                       14

<210> SEQ ID NO 7
<211> LENGTH: 10
<212> TYPE: DNA
<213> ORGANISM: Artificial Sequence
<220> FEATURE:
<223> OTHER INFORMATION: TGF-beta inhibitory element-like sequence
<220> FEATURE:
<221> NAME/KEY: misc_difference
<222> LOCATION: (2)...(3)
<223> OTHER INFORMATION: Each N can be A, G, T or C.

<400> SEQUENCE: 7 gnnttggtga                                                            10

<210> SEQ ID NO 8
<211> LENGTH: 13
<212> TYPE: DNA
<213> ORGANISM: Artificial Sequence
```

-continued

<220> FEATURE:
<223> OTHER INFORMATION: TGF-beta responsive/regulatory element

<400> SEQUENCE: 8
gtgtcaaggg gtc                                                                                      13

<210> SEQ ID NO 9
<211> LENGTH: 838
<212> TYPE: DNA
<213> ORGANISM: Mus musculus

<400> SEQUENCE: 9

| | | | | | | |
|---|---|---|---|---|---|---|
| tctttcttct | cccactatat | tccctgacac | ttaggcttct | gaagatagcc | atttggtctg | 60 |
| aactcataaa | cttatttttc | tagaaaacca | tgcccagtca | taccccttgc | ctgcctggac | 120 |
| cctgaagaca | agttcttaca | taaagagtgc | tgaaaatctt | cctgggaacc | tacatccttg | 180 |
| gctttcatat | ctttcagcca | tcaaaatggc | catctcagtg | accaaagatc | aatgcctgta | 240 |
| tttcagatac | aaaagttgca | cataggaatt | ctgggaggag | aggaggcatt | tcaaatggct | 300 |
| ataagcaccc | ttctcctctc | agtagaagaa | caccaagaga | ctacagcccc | gtaaagaaaa | 360 |
| aaaaaaaaaa | atccaaaaca | aagaaaaaga | aatatttttt | ttaatttcta | ggggcccatg | 420 |
| gtatttgcct | cttgagctat | ttgagtcttg | agaagttttt | atgtcagtag | ccagaactgg | 480 |
| caaagagatt | tttaagaaga | aaagatcaga | gaaataatcg | tttatttcta | agttatattt | 540 |
| catcaggagg | ggtgagaaga | cgatatggag | aaagttttac | ttcttggtgt | tgtgctggaa | 600 |
| acacagcgcc | tttttttttt | ttttcctggc | gagctaaagt | gtgccagctt | tttcagacgg | 660 |
| aggaatgtgg | agtgtcaagg | ggtcaggatc | aatccggtgt | gagttgatga | ggcaggaagg | 720 |
| tggggaggaa | tgtgaggaat | gtccctgttt | gtgtaggact | tcattcagtt | ctttggcgag | 780 |
| ccggctcccg | ggagcgtata | aaagccagcg | ccgcccgcct | agtctcacac | agctcttc | 838 |

We claim:

1. A method for identifying a composition which affects TGF-β induced connective tissue growth factor (CTGF) expression, the method comprising:
   (a) incubating components comprising the composition, TGF-β, and a nucleic acid molecule comprising an expressible nucleotide sequence operably linked to a TGF-β regulatory element (TβRE),
   said TβRE comprising the nucleotide sequence 5'-GTGTCAAGGGGTC-3' (SEQ ID NO: 8),
   wherein the incubating is carried out under conditions and for a time sufficient to allow the components to interact; and
   (b) comparing expression of the expressible nucleotide sequence operably linked to the TβRE in the presence of the composition with the level of expression of the nucleotide sequence in the absence of the composition, wherein a difference in the levels of expression identifies a composition that affects TGF-β induced CTGF expression.

2. The method of claim 1, wherein the composition inhibits CTGF expression.

3. The method of claim 1, wherein the composition stimulates CTGF expression.

4. The method of claim 1, wherein the expressible nucleotide sequence is selected from the group consisting of β-lactamase, chloramphenicol acetyltransferase (CAT), adenosine deaminase (ADA), aminoglycoside phosphotransferase (neo, G418), dihydrofolate reductase (DHFR), hygromycin-B-phosphotransferase (HPH), thymidine kinase (TK), β-galactosidase (β-gal), and xanthine guanine phosphoribosyltransferse (XGPRT).

5. The method of claim 1, wherein said TβRE comprises nucleotides 664 to 698 as set forth in SEQ ID NO: 1.

6. The method of claim 1, wherein said TβRE comprises nucleotides 1 to 897 as set forth in SEQ ID NO: 1.

7. A method of identifying a composition that regulates connective tissue growth factor (CTGF) expression from a TGF-β regulatory element (TβRE), the method comprising:
   (a) incubating a nucleic acid molecule comprising a TβRE comprising the nucleotide sequence 5'-GTGTCAAGGGGTC-3' (SEQ ID NO: 8) operably linked to an expressible nucleotide sequence, and a composition suspected of having the ability to regulate expression of the expressible nucleotide sequence from the TβRE, under conditions and for a time sufficient to allow such expression; and
   (b) comparing the level of expression of the expressible nucleotide sequence in the presence of the composition with the level of expression in the absence of the composition, wherein a difference in the level of expression identifies a composition that regulates CTGF expression from the TβRE.

8. The method of claim 7, wherein said TβRE comprises nucleotides 664 to 698 as set forth in SEQ ID NO: 1.

9. The method of claim 7, wherein said TβRE comprises nucleotides 1 to 897 as set forth in SEQ ID NO: 1.

* * * * *